United States Patent
Gerberding et al.

(10) Patent No.: US 9,233,906 B2
(45) Date of Patent: Jan. 12, 2016

(54) PURIFICATION OF SUCCINIC ACID FROM THE FERMENTATION BROTH CONTAINING AMMONIUM SUCCINATE

(75) Inventors: Steven J. Gerberding, Somerville, MA (US); Ramnik Singh, Winchester, MA (US)

(73) Assignee: Group Novasep SAS (FR)

( * ) Notice: Subject to any disclaimer, the term of this patent is extended or adjusted under 35 U.S.C. 154(b) by 576 days.

(21) Appl. No.: 13/519,491

(22) PCT Filed: Dec. 31, 2010

(86) PCT No.: PCT/US2010/062635
§ 371 (c)(1),
(2), (4) Date: Jun. 27, 2012

(87) PCT Pub. No.: WO2011/082378
PCT Pub. Date: Jul. 7, 2011

(65) Prior Publication Data
US 2012/0289742 A1  Nov. 15, 2012

Related U.S. Application Data

(60) Provisional application No. 61/335,189, filed on Dec. 31, 2009.

(51) Int. Cl.
*C07C 51/43* (2006.01)
*C07C 51/47* (2006.01)
*C12P 7/46* (2006.01)

(52) U.S. Cl.
CPC ............... *C07C 51/43* (2013.01); *C07C 51/47* (2013.01); *C12P 7/46* (2013.01)

(58) Field of Classification Search
CPC .......... C07C 51/41; C07C 51/42; C07C 51/43
See application file for complete search history.

(56) References Cited

U.S. PATENT DOCUMENTS

| | | | |
|---|---|---|---|
| 2,664,441 A * | 12/1953 | Owens et al. ................. | 548/534 |
| 5,034,105 A | 7/1991 | Berglund | |
| 5,068,418 A | 11/1991 | Kulprathipunja et al. | |
| 5,068,419 A * | 11/1991 | Kulprathipanja et al. .... | 562/580 |
| 5,104,492 A | 4/1992 | King et al. | |
| 5,132,456 A | 7/1992 | King et al. | |
| 5,143,833 A | 9/1992 | Datta | |
| 5,143,834 A | 9/1992 | Glassner et al. | |
| 5,168,055 A | 12/1992 | Datta et al. | |
| 5,412,126 A | 5/1995 | King et al. | |
| 5,426,220 A | 6/1995 | Baniel et al. | |
| 5,641,406 A | 6/1997 | Sarhaddar et al. | |
| 5,770,435 A | 6/1998 | Donnelly et al. | |
| 5,786,185 A | 7/1998 | Tsao et al. | |
| 5,817,238 A | 10/1998 | Makino et al. | |
| 5,958,744 A | 9/1999 | Berglund et al. | |
| 6,159,738 A | 12/2000 | Donnelly et al. | |
| 6,160,173 A | 12/2000 | Eyal et al. | |
| 6,265,190 B1 | 7/2001 | Yedur et al. | |
| 6,280,985 B1 | 8/2001 | Caboche et al. | |
| 6,284,904 B1 * | 9/2001 | Ponnampalam ............... | 554/193 |
| 6,319,382 B1 | 11/2001 | Norddahl | |
| 6,455,284 B1 | 9/2002 | Gokram et al. | |
| 7,223,567 B2 | 5/2007 | Ka-Yiu | |
| 7,238,837 B1 | 7/2007 | Eyal et al. | |
| 7,439,392 B2 | 10/2008 | Kulprathipunja | |
| 7,563,606 B2 | 7/2009 | Aoyama et al. | |
| 7,763,447 B2 | 7/2010 | Murage et al. | |

(Continued)

FOREIGN PATENT DOCUMENTS

CN  101215583 A * 7/2008
WO  8905861 A1  6/1989

(Continued)

OTHER PUBLICATIONS

Levin, Shula Levin's WebSite of HPLC and LC-MS,2007, pp. 1-8, recovered from http://www.forumsci.co.il /HPLC/ion_chrm.html on Nov. 4, 2014).*
Bechthold, I. et al. "Succinic acid: a new platform chemical for bio-based polymers form renewable resources" Chemical Engineering & Technology, 2008, pp. 647-654, vol. 5.
Davison, B. H. "Succinic acid adsorption form fermentation broth and regeneration" Applied Biochemistry and Biotechnology, 2004, pp. 113-116, vol. 113-115.
Delhomme, C. "Succinic acid from renewable resources as a C4 building-block chemical—a review of the catalytic possibilities in aqueous media" Green Chemistry, 2009, pp. 13-16, vol. 11.
Hong, Y. K. et al "Reactive extraction of succinic acid with triprophylamine (TPA) in various diluents" Bioprocess Engineering, 2000, pp. 281-284, vol. 22.
Hong, Y. K. et al Equillibrium studies on reactive extraction of succinic acid from aqueous solutions with tertiary amines. BioProcess Engineering, 2000, pp. 477-481, vol. 22.

(Continued)

*Primary Examiner* — Paul A Zucker
(74) *Attorney, Agent, or Firm* — Fox Rothschild LLP; Gerard P. Norton; Robert N. Henrie, II

(57) ABSTRACT

This present invention relates to the processes for the purification of succinic acid from a fermentation broth containing ammonium succinate. The process for the purification of succinic acid described in this invention involves the use of ion exchange resins for splitting the ammonium succinate in the fermentation broth. During the passage of the fermentation broth through a cationic ion exchange resin, the ammonium succinate is split into ammonium cation and the succinate anion. The proton on the resin surface is exchanged for the ammonium ions and the succinate anion is reduced to succinic acid with the protons released from the ion exchange resin. The bound ammonium is released from the resin with the addition of a strong acid such as sulfuric acid and thereby the ion exchange resin is regenerated for subsequent use. The ammonium sulfate by-product resulting from the regeneration step of this process can be used as a source of fertilizer. This process for the separation of succinic acid from the fermentation broth containing ammonium succinate can also be carried out with an anionic ion exchange resin wherein the succinate anion is retained on the surface of the ion exchange resin and subsequently released from the ion exchange resin during the regeneration step.

17 Claims, 14 Drawing Sheets

(56) References Cited

U.S. PATENT DOCUMENTS

| | | |
|---|---|---|
| 7,829,316 B2 | 11/2010 | Koseki et al. |
| 7,833,763 B2 | 11/2010 | Yamagishi |
| 2006/0276674 A1* | 12/2006 | Kushiku et al. ............... 562/562 |
| 2007/0011294 A1 | 1/2007 | Ohara |
| 2009/0137825 A1 | 5/2009 | Baudin et al. |
| 2009/0137843 A1 | 5/2009 | Isotani et al. |
| 2010/0184171 A1 | 7/2010 | Jantama et al. |
| 2010/0297715 A1 | 11/2010 | Dahay et al. |
| 2012/0238722 A1* | 9/2012 | Van De Graaf et al. ...... 528/272 |

FOREIGN PATENT DOCUMENTS

| | | |
|---|---|---|
| WO | 9830712 A1 | 7/1998 |
| WO | 2007040458 A1 | 4/2007 |
| WO | 2008115958 A1 | 9/2008 |
| WO | 2009065778 A1 | 5/2009 |
| WO | 2009065780 A1 | 5/2009 |
| WO | 2009082050 A1 | 7/2009 |
| WO | 2010115067 A1 | 10/2010 |

OTHER PUBLICATIONS

Hong, Y. K. et al "Extraction of succinic acid with 1-octanol/n-heptane solutions of mixed tertiary amine" Bioprocess Engineering, 2000, pp. 535-538, vol. 23.

Hong, S. H. et al "Metabolic flux analysis for succinic acid production by recombinant *Escherichia coli* with amplified malic enzyme activity" Biotechnology and Bioengineering, 2001, pp. 89-95, vol. 74.

Hong, Y. K. et al "Selective extraction of succinic acid from binary mixture of succinic acid and acetic acid" Biotechnology Letters, 2010, pp. 871-874, vol. 22.

Huh, Y. S. et al "Effective purification of succinic acid form fermentation broth produced by Mannheimia succiniproducens" Process Biochemistry, 2006, pp. 1461-1465, vol. 41.

Inci, I. et al "Linear salvation energy relationship modeling and kinetic studies on reactive extraction of succinic acid by tridodecylamine dissolved in MIBK" Biotechnology Progress, 2007, pp. 1171-1179, vol. 23.

Jantama, et al "Combining metabolic engineering and metabolic evolution to develop nonrecombinant strains fo *Escherichia coli* C that produce succinate and malate" Biotechnology and Bioengineering, 2008, pp. 1140-1153, vol. 99.

Jantama, et al "Eliminating side products and increasing succinate yileds in engineered strains of *Escherichia coli* C" Biotechnology and Bioengineering, 2008, pp. 881-893, vol. 101.

Jun, Y. S. et al "Kinetics of the extraction of succinic acid with tri-n-octylamine in 1-Octanol solution" Biotechnology Progress, 2005, pp. 1673-1679, vol. 21.

Kurzrock, T. et al "Recovery of succinic acid from fermentation broth" Biotechnology Letters, 2010, pp. 331-339, V. 32.

Li, Q. et al "pH Neutralization while succinic acid adsorption onto anion exchange resins" Applied Biochemistry and Biotechnology, 2010, pp. 438-445, vol. 160.

Ullmann's Encyclopedia of Industrial Chemistry, (2003), wiley-VCH Verlag GmbH & Co., KGa-A, Weinheim, vol. 18, p. 344.

* cited by examiner

PURIFICATION OF SUCCINIC ACID FROM THE FERMENTATION BROTH CONTAINING AMMONIUM SUCCINATE

CROSS-REFERENCE TO RELATED APPLICATION

The application is the U.S. national stage application of International Patent Application No. PCT/US2010/062635, which claims the priority of the U.S. Provisional Application Ser. No. 61/335,189, filed on Dec. 31, 2009.

BACKGROUND OF THE INVENTION

The advances in our ability to do genetic manipulations in the microbial biochemical pathways accompanied by improvements in fermentation process technology have made it possible to produce commercially significant quantities of succinic acid using agricultural and forestry renewable feedstocks. All of the microbial organisms engineered to produce succinic acid reach their maximum productivity within a narrow pH range. For this reason, during the fermentative production of succinic acid, the pH of the fermentation medium is kept at near neutral pH by means of compensating the drop in the pH of the medium with the addition of certain neutralizing base compounds. This results in the accumulation of succinic acid in the fermentation medium in the form of a basic salt of succinic acid. Thus depending on the nature of the neutralizing base used, the succinic acid accumulates in the fermentation medium as sodium or potassium or calcium or ammonium succinate. Therefore, further downstream processing of the fermentation broth is required to extract the pure succinic acid from the fermentation broth containing a basic salt of succinic acid. A downstream processing method that recovers succinic acid from the fermentation broth along with the release of the neutralizing agent is desirable in the succinic acid manufacturing in a commercially successful way.

Several different approaches have been followed to purify the organic acids from fermentation broth including precipitation, steam distillation, liquid-liquid extraction, countercurrent extraction, esterification, and a combination of electrodialysis and extraction. In general, the fermentation broth is subjected to microfiltration and ultrafiltration to remove cellular debris before subjecting to any specific process to recover succinic acid.

A number of methods have been reported for the recovery of succinic acid from the fermentation broth containing a basic salt of succinic acid. All these known processes for the recovery of succinic acid from fermentation broth are found to be lengthy and expensive for the production of succinic acid from fermentation broth in a commercial scale.

U.S. Pat. No. 5,034,105 assigned to Michigan Biotechnology Institute provides a process for preparing succinic acid from a fermentation broth containing sodium succinate. This process comprises steps of subjecting the broth to conventional electrodialysis to prepare an aqueous but unsaturated succinate solution, subjecting the unsaturated succinate solution to water splitting electrodialysis to produce a supersaturated succinic acid solution and then crystallizing the succinic acid from the supersaturated solution. This process is not suitable for the purification of succinic acid from the fermentation broth in a large scale as evidenced by the lack of commercial exploitation of this process during the last twenty years of its existence.

U.S. Pat. Nos. 5,958,744 and 6,265,190 assigned to Applied CarboChemicals provide a method for recovering succinic acid from fermentation broth containing calcium succinate. According to this method, the fermentation broth is acidified with the addition of sulfuric acid. As a result of this acidification process, the succinate anion is released from calcium succinate, gets protonated and the resulting succinic acid precipitates out of the fermentation broth. The resulting precipitate is filtered and washed with alcohol to obtain succinic acid. It remains to be seen whether the succinic acid thus produced would satisfy the required level of purity. In addition, the disposal of calcium sulfate (gypsum) poses an environmental concern.

A recently published United States Patent Application Publication No. U.S. 2010/0297715 assigned to Roquette Freres describes a process for separating and purifying succinic acid from fermentation broth containing magnesium succinate. The separation process described in this published patent application is complicated and expensive. The separation process involves bipolar electrodialysis, evaporative crystallization, and high temperature treatment to recover the reagents for recycling purpose. As a result of these process steps involved in the recovery of succinic acid from fermentation broth, the cost of production of succinic acid using this process in a commercial scale is going to be very expensive.

A recent U.S. Patent Application Publication No. 2009/0137825 assigned to BASF has disclosed a reactive distillation process for esterifying succinic acid from fermentation broth. However, this Patent Application Publication does not provide any actual method for recovering succinic acid from fermentation broth that has been reduced to practice.

A number of efforts have also been made to recover carboxylic acid from the fermentation broth using the process involving ion exchange resins. The ion exchange resins are used in two different ways in the separation of carboxylic acids from the fermentation broth comprising carboxylic acid salts. According to one method, the ion exchange resins are used in the ion exclusion mode. In another method, the ion exchange resins chemically interact with the salts of carboxylic acid in the fermentation broth to achieve the separation of the carboxylic acid from the carboxylic acid salts. The first method is referred as ion exclusion chromatography and the second method is known as ion exchange chromatography.

U.S. Pat. No. 5,132,456 provides a method for recovering carboxylic acid from aqueous feedstock in which the carboxylic acid is first adsorbed onto a basic solid adsorbent or moderately basic ion exchange resin, and then released from the adsorbent by treating it with aqueous alkylamine or ammonia leading to the formation of alkylammonium or ammonium carboxylate which is decomposed to the desired carboxylic acid and the alkylamine or ammonia.

U.S. Pat. No. 5,143,834 provides a method for recovering succinic acid from fermentation broth using desalting electrolysis and water-splitting electrolysis followed by a strongly acidic ion exchanger to remove any sodium or other cations and a weakly basic ion exchanger in the free base form to remove any sulfate ion or sulfuric acid to obtain a highly purified succinic acid product.

U.S. Pat. No. 5,168,055 provides a method for recovering succinic acid from fermentation broth containing calcium succinate. In the first stage, the fermentation broth is acidified to release succinic acid from calcium succinate. The succinic acid thus released is passed through a strongly acidic ion exchange resin and a weakly basic ion exchanger to obtain a highly purified succinic acid product. During the passage through the cation exchanger, calcium and other cations are removed. During the subsequent passage through a second column containing anionic exchange resin, the anionic impurities such as sulfate and other nitrogenous impurities are removed.

U.S. Pat. No. 5,641,406 provides a method for extracting pure lactic acid from fermentation liquors containing lactic acid salt by ion exchange chromatography on a strongly acidic cation exchange resin. In the first stage of this method, the lactic acid salt is converted into free acid by means of genuine ion exchange in one or more "preliminary columns" containing weakly acidic cation exchanger in H+ form. In the second stage of this method, the free lactic acid is separated from the carbohydrates and other impurities present in the fermentation solution by using a strongly acidic ion exchange resin in one or more "separation columns." The process is carried out at temperature higher than 50° C. and preferably between 70° C. to 80° C.

U.S. Pat. Nos. 5,068,418 and 5,068,419 provide a method for the separation of an organic acid from a fermentation broth using an adsorbent comprising a water-insoluble macro reticular or gel type weakly basic anionic exchange resin possessing tertiary amine or pyridine functional groups or a strongly basic anionic exchange resin possessing quaternary amine functional groups. The organic acid is desorbed from the ion exchange resin with water or dilute inorganic acid like sulfuric acid.

U.S. Pat. No. 5,786,185 provides an improved fermentation process for producing lactic acid. As per this process, the fermentation broth comprising free lactic acid is contacted with an effective amount of solid-phase polymer containing pyridine groups to adsorb the lactic acid as it is accumulated and returning the treated fluid fermentation broth back to the fermentation vessel.

U.S. Pat. No. 6,160,173 describes the use of water immiscible anion exchanger to recover lactic acid from a feed solution comprising lactic acid and lactic acid salt mixture. In the first step, the feed solution is contacted with an anion exchanger and an anion exchanger-lactic acid adduct is formed. From this anion exchanger-lactic acid adduct, the lactic acid ester or amine is produced through condensation reaction.

U.S. Pat. No. 6,280,985 assigned to Roquette Freres discloses a method for separation and purification of lactic acid from a fermentation broth using an ion exclusion chromatography with cation exchange resin. This method involves several unit operations besides chromatographic separation through a cation exchange resin. Thus, the original fermentation broth is concentrated in the first stage followed by acidification with concentrated acid to reach a free lactic acid/ammonium lactate ratio of 85/15. The acidified broth is passed through cation exchange resin of the polystyrene sulfonic acid type cross-linked with at least 4% of divinylbenezene to obtain a fraction that has a maximum of 25% lactic acid salts. All the impurities such as unconsumed sugars and proteins and of the inorganic acid salts of the type with polyvalent ions calcium, magnesium and any base corresponding to any dissociated lactic acid salt in the fermentation broth are removed in the first fraction by elution with water. The next fraction contains lactic acid in the free from and at most 25% by dry weight of lactic acid salt present in the original fermentation broth. This fraction is further subjected to bipolar fractionating electrodialysis to obtain purified, concentrated lactic acid.

U.S. Pat. No. 6,284,904 discloses a method for purification of organic acids using anion exchange chromatography in which the organic acid such as succinic acid is bound to the anion resin followed by displacement of the organic acid by a strong basic anion solution or an acid having a pKa lower than that of the organic acid bound to the anion resin.

U.S. Pat. No. 6,319,382 teaches a method for recovering lactic acid from a fermentation broth containing ammonium lactate wherein the said method comprises steps of nanofiltration, ion exchange using a chelating resin that primarily removes the divalent cations such as calcium and magnesium and a final two-step electrodialysis procedure.

U.S. Pat. No. 7,238,837 provides a method for recovering lactic acid from aqueous solution containing lactate salt with a conversion efficiency of 56% of the sodium lactate to lactic acid through a method using cation exchange resin.

U.S. Pat. No. 7,439,392 provides a method for separating citric acid from a fermentation broth by using an adsorbent comprising a water-insoluble, macro reticular or gel, strongly or weakly basic anionic exchanger resin possessing quaternary or tertiary amine functional groups, anionic exchange resin having a cross-linked acrylic or styrene resin matrix and a desorbent comprising water or dilute sulfuric acid. The pH of the feed is maintained below the first ionization constant (pKa1) of citric acid to maintain selectivity.

U.S. Patent Application Publication No. 2006/0276674 describes a method for purifying succinic acid from fermentation broth. According to this method, the impurities in a succinic acid containing liquid could be efficiently removed by combining ion-exchange using a certain amount of an H-type strongly acidic cation-exchange resin with a crystallization process to produce high purity succinic acid in good yield.

International application No. WO 2007/040458 published under the Patent Cooperation Treaty provides a method for removing cationic and anionic impurities using ion exchange resin in the process of recovering lactic acid from fermentation broth containing lactic acid. The ammonium ions were removed using a strong cationic exchange resin and the anion exchange resin was used to remove sulfate impurity.

International patent application No. WO 98/30712 published under the Patent Cooperation Treaty and assigned to Amylum Belgium provides a method for recovering crystalline aspartic acid from ammonium aspartate using a cation exchanger resin.

Various methods tested so far to recover organic acids from fermentation broth have presented limitations and thus offer opportunities for improvement. Thus the objective of the present invention is to provide a commercially viable process for recovering succinic acid from a fermentation broth comprising ammonium succinate.

SUMMARY OF THE PRESENT INVENTION

Figure 1:
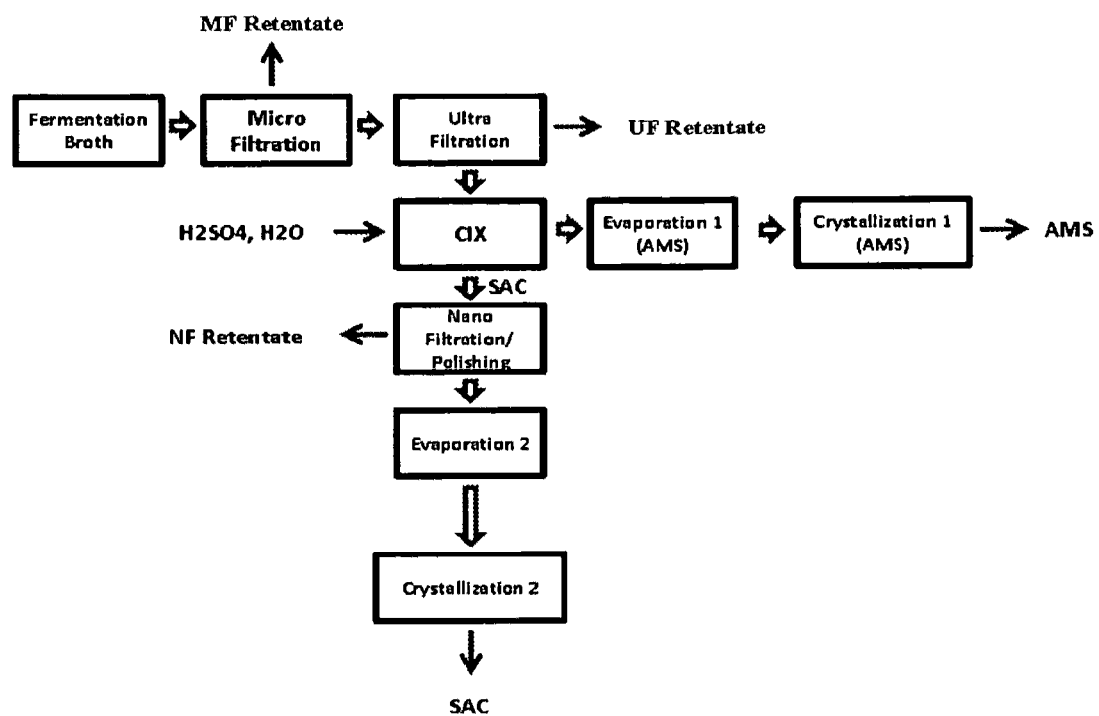
FIG. 1 Block flow diagram for succinic acid downstream recovery process. The fermentation broth is subjected to microfiltration and ultra filtration before subjecting it to continuous ion exchange (CIX) process. The succinic acid fraction (SAC) from continuous ion exchange process is subjected to nanofiltration/polishing steps before evaporation and subsequent crystallization steps to recover succinic acid in the form of crystals. The ammonium sulfate (AMS) fraction from the continuous ion exchange process is subjected to evaporation process to recover ammonium sulfate crystals.

The objective of the present invention is to recover at least 90% (w/w) of the succinic acid from a fermentation broth containing 2 to 10% succinic acid in the form of a neutral salt of succinic acid. The succinic acid thus recovered would have the appearance of white crystals and has a purity of 99.5% (w/w) or more. The preferable sulfate concentration in the succinic acid fraction is below 100 ppm. The most preferable sulfate concentration in the succinic acid fraction obtained as per the process of the present invention is below 30 ppm. The present invention provides processes for preparing succinic acid from an ammonium salt of succinic acid present in the fermentation broth. The processes according to this invention involve the use of ion exchange resins in the recovery of succinic acid in a pure form in commercially significant quantities. Although the present invention describes in detail the process for recovering succinic acid from fermentation broth containing ammonium succinate, a person knowledgeable in the art of producing organic acid from biological feedstock will be able to apply the chromatographic processes of the present invention for recovering succinic acid from the fermentation broth containing succinic acid in the salt forms other than ammonium succinate as well as in recovering any other organic acid salts from a fermentation broth in a commercially significant quantities in a cost-effective manner.

In the present invention, the ion exchange resin is used to mediate a salt splitting reaction for the purpose of releasing the succinic acid from ammonium succinate present in the fermentation broth. The salt splitting reaction according to the present invention can be achieved using either an anionic or a cationic ion exchange resin.

In one aspect of the present invention, the ion exchange process for the purification of succinic acid from a solution containing ammonium succinate uses cationic ion exchange resin. The process for purifying succinic acid using cationic ion exchange resin from an aqueous solution containing ammonium succinate comprises the following steps: (a) providing an aqueous solution comprising the ammonium salt of succinic acid; (b) contacting the cationic ion exchange resin with aqueous solution comprising the ammonium salt of succinic acid; (c) converting the ammonium salt of succinic acid to succinic acid and ammonium cation in aqueous solution; (d) separating the ammonium cation from the aqueous solution, leaving the succinic acid in aqueous solution; and (e) recovering the succinic acid in aqueous solution. Upon contact with cationic ion exchange resin, the ammonium succinate is split into ammonium ion and succinate ion. The ammonium ion thus produced from salt splitting reaction binds to the surface of the cationic resin and thereby the cationic ion exchange resin is converted into ammonium salt form. Subsequently, the cationic ion exchange resin in its ammonium salt form is regenerated to its original form by washing it with strong acid such as hydrochloric acid or sulfuric acid. The ammonium salt resulting from the regeneration step of the cationic ion exchange resin can be put either into commercial use or recycled to the fermentation process. In order to achieve the best efficiency for the separation of succinic acid from an aqueous solution containing ammonium succinate, a continuous process using cationic ion exchange resin is preferred over the batch process involving a conventional column chromatography using cationic ion exchange resin.

In yet another embodiment of the present invention, the ion exchange process based on the use of anionic ion exchange resin is used to recover the succinic acid from an aqueous solution containing ammonium succinate. Just as is the case with the ion exchange chromatography involving cationic ion exchange resin, the purification of the succinic acid from an aqueous solution containing ammonium succinate using anionic ion exchange resin involves salt splitting reaction. Ammonium succinate is split into ammonium cation and succinate anion on the surface of the anionic ion exchange resin and the succinate anion thus produced is exchanged for the anionic species on the surface of the resin. Thus the succinic anion is captured on the surface of the resin while the anion released from the anionic ion exchange resin combines with the ammonium cation to produce a new ammonium salt in place of the original ammonium succinate salt in the aqueous solution. The newly formed ammonium salt is eluted out of the ion exchange column in the raffinate fraction. The succinate ion bound to the anionic ion exchange resin is subsequently released from the ion exchange resin with the addition of a strong inorganic acid. This washing step involving strong inorganic acid besides releasing the succinic acid from the ion exchange resin, regenerate the anionic ion exchange resin to its original form so that it can mediate salt splitting reaction once again with the addition of new aqueous solution containing ammonium succinate.

The ion exchange process for the recovery of succinic acid from the fermentation process containing ammonium succinate is operated either in the batch mode or in a continuous mode. The operation of this ion exchange process in the continuous mode is preferred over the batch mode.

The fermentation broth used in this continuous or batch process involving ionic exchange resins may be processed prior to the use in the ion exchange process in one or other way in order to improve the recovery of succinic acid. In one aspect of the present invention, the fermentation broth is subjected to dehydration process involving organic solvents. In another aspect of the present invention, the fermentation broth containing ammonium succinate is subjected to microfiltration and ultrafiltration in order to remove the particulate matter in the fermentation broth with the goal of improving the recovery of succinic acid in the acid form.

The succinic acid obtained from the ion exchange process is subjected to crystallization process to obtain succinic acid in a crystalline form. The ammonium sulfate recovered as a byproduct in the ion exchange process is also subject to crystallization or concentration process.

In another embodiment of the present invention, the succinic acid recovered from the ion exchange process is subjected to polishing process to improve the quality of the succinic acid recovered from the fermentation broth. In one aspect of the present invention, the succinic acid recovered from the ion exchange process is subjected to nanofiltration so that the succinic acid crystals obtained after the nanofiltration process has desirable color and minimal level of contaminants.

DETAILED DESCRIPTION OF THE INVENTION

FIG. 1 provides the block flow diagram for the recovery of succinic acid from the fermentation broth comprising ammonium succinate as described in this present invention. A number of microorganisms have been reported to produce significant quantities of succinic acid during their fermentative growth on biological feedstocks. Some of these microorganisms have been genetically modified to achieve succinic acid production at commercially significant quantities. For examples, the KJ122 strain of *Escherichia coli* described in the International Patent Applications published under Patent Cooperation Treaty with the publication Nos. WO 2008/115958 and WO 2010/115067 is reported to produce commercially significant quantities of succinic acid during its fermentative growth. KJ122 strain was derived from *E. coli* C strain (ATCC 8739) through a number of rationally designed genetic manipulations and the process of metabolic evolution at several different stages as described by Jantama et al (2008a, 2008b).

KJ122 strain of *E. coli* is ideal for the production of succinic acid through fermentative pathway. KJ122 is reported to have the capacity to produce 70 to 90 grams of succinic acid per liter in a fermentation vessel. Besides KJ122, the other *E. coli* strains genetically modified to produce succinic acid as described in the U.S. Pat. Nos. 5,770,435, 6,159,738, 6,455,284 and 7,223,567 and U.S. Patent Application Publication No. 2007/011294 are also useful for producing succinic in commercially significant quantities. The fermentation broth from all these stains of *E. coli* containing succinic acid in the form of neutral salt of succinic acid is suitable for use in the present invention.

Besides these genetically modified *E. coli* strains, a number of naturally occurring succinic acid producing microorganism have also been identified and developed for the fermentative production of succinic acid in commercially significant quantities. For example, the international patent applications published under Patent Cooperation Treaty with Publication Nos. WO 2009/065778 and WO 2009/065780 describe the succinic acid producing strains of *Aspergillus niger* and *Saccharomyces cerevisiae*. The list of other microorganisms that have been reported to produce succinic acid in significant quantities includes *Actinobacillus succinogens, Mannheimia succiniproducens, Corynebacterium glutamicum, Brevibacterium flavum* and *Anaerobiospirilum succiniproducens*. The succinic acid produced by any of these microorganisms during their fermentative growth can be recovered at a high level of purity using one or more of the processes described in the present invention.

Due to the acidic nature of the succinic acid, a continued accumulation of succinic acid in the microbial growth medium is expected to decrease the pH of the culture medium and ultimately causing a reduced growth rate of the organism and the succinic acid yield. This limitation is overcome by means of adding certain pH neutralizing bases to the microbial growth medium on a need basis. The addition of neutralizing bases to the microbial growth medium results in the accumulation of succinic acid in the form of a neutral salt. Thus when ammonium hydroxide is used as a base to neutralize the decrease in pH due to succinic acid production, ammonium succinate accumulates in the fermentation vessel.

At the end of the fermentation run, the broth contains salts of succinic acid, heavy metals, coloring matter, metabolic by-products, cells and cell fragments of the microorganisms and inorganic salts. Therefore, direct use of the fermentation broth is not possible and further processing steps are required to extract pure succinic acid from the fermentation broth.

In the first step of the process for recovering pure succinic acid from the fermentation broth, it is desirable to concentrate the broth by extracting water. This concentration step would reduce the volume of the fluid to be processed and ultimately help in reducing the cost towards each of the subsequent unit operations required to recover pure succinic acid. The fermentation broth containing salts of succinic acid can be concentrated by means of removing significant amount of water using low molecular weight secondary and tertiary amines such as triethylamine, diisopropyl amine, N, N-diethylamine and mixtures thereof. At 30° C. to 50° C. temperature range, these organic amines can extract large amounts of water from dilute aqueous solutions such as fermentation broth containing salts of succinic acid. At this low temperature range, the organic amine phase contains 20-35% water and a much reduced quantity of fermentation salts. Water can be phased out of the amine by raising the temperature and thereby allowing the amine to be recycled and reused to extract additional water. By means of using this approach, it is possible to extract 82.5% of water from a fermentation broth containing 3% ammonium succinate using conventional multistage, countercurrent extraction procedure leading to the production of a five-fold concentrated fermentation broth containing 15% ammonium succinate.

In the practice of the present invention, the fermentation broth comprising salts of succinic acid is clarified to get rid of particulate matter present in the fermentation broth. The cellular and protein components in the fermentation broth can be removed by high temperature treatment at 80° C. to 90° C. The high temperature treatment can be accompanied by an alkaline treatment to kill the microorganism and to coagulate the proteins. The insoluble materials resulting from these high temperature and alkaline treatments can be removed through filtration or centrifugation.

The fermentation broth resulting from the high temperature and alkaline treatment can further be clarified using microfiltration and/or ultrafiltration devices. The techniques for the microfiltration and ultrafiltration of microbial fermentation broth are well known in the art of industrial microbiology. The membranes suitable for the microfiltration and the ultrafiltration of microbial fermentation broth are commercially available from a number of suppliers. A centrifugation step could replace the microfiltration step. The supernatant form the centrifugation step can be subjected to ultrafiltration step. The retentate from the these filtration processes is discarded or recycled and the permeate enriched in succinic acid salt is used in the next stage as a source for the purification of succinic acid using ion exchange resins. The permeate from the microfiltration and/or ultrafiltration process steps can optionally be passed through a chelating resin which primarily binds divalent ions such as calcium and magnesium as described in U.S. Pat. No. 6,319,382 before treating it with ion exchange resins.

As a way of explaining the process for recovering succinic acid from fermentation broth according to the present invention in a clear manner, the following definitions of the various terms used in describing the invention are provided at the outset.

"Chromatography" refers to any analytical techniques used for the chemical separation of mixtures and components that relies upon selective attraction among the components of a mixture to a solid phase. Examples include adsorption chromatography, ion exchange chromatography, and ion exclusion chromatography. This present invention is focused on the use of ion exchange chromatography and does not involve ion exclusion chromatography. As a way of differentiating between the ion exclusion chromatography and ion exchange chromatography, the following definitions are provided.

Ion exclusion is the term used to describe the mechanism by which ion-exchange resins are used for the fractionation of neutral and ionic species. The ionic compounds in a sample to be fractionated are rejected by the resin and they are eluted in the void volume of the column. Nonionic or weakly ion substances penetrate into the pores of the packing and thereby the separation is achieved as they partition between the liquid inside and outside the resin particles. Ion exclusion chromatography is also referred to by several other names, including ion exclusion partition chromatography, ion chromatography-exclusion mode, and Donnan exclusion chromatography.

The term ion-exchange or ion exchange chromatography as used in this invention is used to describe the mechanism by which the neutral chemical molecule upon its interaction with an ion exchange resin is split into its charged components. This phenomenon of generating the charged species from a neutral molecule is defined as salt-splitting. Based on the nature of the resin being used, one of the ionic components resulting from the salt-splitting reaction bind to the resin and the other molecule flows away from the resin particles. When a cation exchange resin is used, the positively charged ion resulting from the salt-splitting reaction would be bound to the ion exchange resin and the negatively charged species flows away from the resin. On the other hand when an anion exchange resin is used, the negatively charged ion resulting from the salt-splitting reaction is bound to the anion exchange resin and the positively charged ion species flows away from the resin. This ion exchange process of the present invention is explained below with the process for recovering succinic acid from fermentation broth containing ammonium succinate.

When ammonium succinate molecule is in contact with a cationic ion exchange resin, the ammonium succinate molecule is split into positively charged ammonium cation and the negatively charged succinate anion. The ammonium cation binds to the resin replacing a hydrogen ion from the resin surface. The hydrogen ion thus released from the surface of the cation ion exchange resin combines with the succinate anion to produce succinic acid molecule. The ammonium ion bound to the resin surface is subsequently released from the resin surface with a strong acid which also regenerates the ion exchange resin to its original form.

When ammonium succinate molecule is in contact with an anionic ion exchange resin, the ammonium succinate molecules are split into positively charges ammonium cation and the negatively charged succinate anion. The negatively charged succinate anion binds to the resin surface and thereby replacing a negatively charged anion such as sulfate form the surface of the resin. The negatively charged sulfate anion released from the resin surface reacts with ammonium cation to produce ammonium sulfate which comes out in the raffinate fraction. The succinate ion bound to the resin surface is released from the resin surface with the strong acid treatment which releases the succinate ion from the surface of the resin as succinic acid besides regenerating the resin to its original form. Sulfuric acid and hydrochloric acid are suitable for this purpose.

"Adsorbent" is used herein generically to refer to the solid phase used in chromatography for which the mobile phase components exhibit a selective affinity. Because such affinity can take a variety of forms other than adsorption, including size exclusion, the term refers to solid phases that adsorb the components of a mixture and to solid phases that do not technically adsorb components from mobile phase, but which nevertheless behave like an adsorbent by slowing the migration velocity of one component relative to another in a chromatographic system. The ion exchange resins used in the present invention is an example for adsorbent. The special ability of the ion exchange adsorbent of the present invention is that it can chemically split a neutral molecule adsorbed on its surface into its ionic component and chemically bind one of the ionic components on the basis of the charge.

The term "purified" refers to a component or fraction when its relative concentration (weight of component or fraction divided by the weight of all components or fractions in the mixture) is increased by at least 20%. A component or fraction can also be said to be purified when the relative concentration of components from which it is purified (weight of component or fraction from which it is purified divided by the weight of all components or fractions in the mixture) is decreased by at least 20%.

A "feed mixture" is a mixture containing one or more extract components and one or more raffinate components to be separated by the chromatographic process. The term "feed stream" indicates a stream of a feed mixture which passes to the adsorbent used in the process.

An "extract component" is a component or type that is more selectively adsorbed by the adsorbent while "raffinate component" is a compound or type of compound that is less selectively adsorbed.

The term "desorbent material" shall mean generally a material capable of desorbing an extract component. In other words, the charged material bound to the ion exchange resin is released from the surface of the ion exchange resin by a desorbent material. The term "desorbent stream" or "desorbent input stream" indicates the stream through which desorbent material passes to the adsorbent.

The term "raffinate stream" or "raffinate output stream" means a stream through which a raffinate component is removed from the adsorbent. The composition of the raffinate stream can vary from essentially 100% desorbent material to essentially 100% raffinate component.

The term "extract stream" or "extract output stream" shall mean a stream through which an extract material has been desorbed by a desorbent material is removed from the adsorbent. The composition of the extract stream can vary from essentially 100% desorbent material to essentially 100% extract components.

At least a portion of the extract steam and preferably raffinate stream coming out of the chromatographic column is passed through a separation device such as a fraction collector where at least a portion of desorbent material is separated to produce an extract product and a raffinate product. The terms "extract product" and "raffinate product" means products produced by the process containing, respectively an extract component and a raffinate component in higher concentrations than those found in the extract stream and the raffinate stream.

Certain characteristics of adsorbents have been recognized to be essential for the successful operation of any chromatographic process. The desirable features of adsorbent are: (1) Adsorptive capacity of the adsorbent, (2) The selectivity of adsorbent and (3) Rate of adsorption and desorption.

Capacity of the adsorbent to adsorb a specific volume of extract component is an important feature. The higher the adsorbent's capacity for an extract component the better is the adsorbent. With increased adsorptive capacity for an adsorbent, it is possible to reduce the amount of adsorbent needed to separate an extract component of known concentration contained in a particular feed mixture.

The second necessary adsorbent characteristic is the ability of the adsorbent to separate components of the feed. This ability of the adsorbent to separate one component from the other component is referred as adsorptive selectivity. Relative selectivity can be expressed not only for one feed component as compared to another but can also be expressed between any feed mixture component and the desorbent material. The adsorbent selectivity as used here is defined as the ratio of the two components on the adsorbed phase over the ratio of the same two components in the unadsorbed phase at equilibrium conditions. Where selectivity of two components approach 1.0 there is no preferential adsorption of one component by the adsorbent with respect to the other; they both are adsorbed (or nonadsorbed) to about the same degree with respect to each other. As the selectivity becomes less than or greater than 1.0 there is a preferential adsorption of one component with respect to other. While separation of an extract component from a raffinate component is theoretically possible when the selectivity of the adsorbent for the extract component with respect to the raffinate component is greater than 1, it is preferred that selectivity approach a value of 2.

The third desirable feature of an adsorbent is related to the rate of exchange of extract component by the adsorbent. An ideal adsorbent must be able not only to adsorb the extract component at a greater rate but at the same time should have the capacity to desorb the bound extract component easily in the presence of an appropriate desorbent. Faster rates of exchange reduce the amount of desorbent material needed to remove the extract component and therefore permit a reduction in the operating cost of the process. With the faster rates of exchange, less desorbent material has to be pumped through the process and separated from the extract stream for reuse in the process.

In order to select an adsorbent suitable for a particular separation protocol, a set of adsorbents can be subjected to a pulse test using a dynamic testing apparatus. By means of conducting a pulse test, one can determine the characteristic features of selected adsorbents with reference to their adsorption capacity, selectivity and exchange rate.

The apparatus for conducting the pulse test can have a simple configuration. The apparatus consists of an adsorbent chamber filled with a test adsorbent. The adsorbent chamber may be a straight column or a helical column. The adsorbent chamber may be operated at the ambient temperature or may be kept inside a temperature controlled environment. It is necessary to run the chromatographic separations under optimal conditions. Optimal temperature of the adsorbent chamber will provide an increase in the separation capacity of the resin. An optimal temperature will also improve the useful capacity of the adsorbent. Besides the temperature environment, the adsorbent column can be connected to a pressure control equipment to operate the adsorbent chamber at a constant predetermined pressure. Quantitative and qualitative analytical instruments such as refractometers, polarimeters, and UV/visible spectrophotometers can be attached to the outlet line of the adsorbent chamber and used to detect quantitatively one or more components in the effluent stream leaving the adsorbent chamber.

The adsorbent in the adsorbent chamber is filled to equilibrium with a particular desorbent material by passing the desorbent material through the adsorbent chamber. At a convenient time, a pulse of feed containing known concentration of a tracer and of a particular extract component or of a raffinate components or both, all diluted in desorbent, is injected for a duration of several minutes. Tracer is a component known to have defined interaction with the adsorbent. Desorbent flow is resumed, and the tracer and the extract component or the raffinate component (or both) are eluted. The effluent can be analyzed on-stream or alternatively, effluent samples can be collected periodically and later analyzed.

From the results of the pulse test, the adsorption capacity of an adsorbent, selectivity of an adsorbent for a particular extract component and the rate of exchange of a particular extract component on the surface of the adsorbent can be determined. By means of determining the amount of extract component in the feed mixture and in the raffinate stream and taking the amount of adsorbent in the adsorbent chamber into calculation, it is possible to determine the adsorption capacity of a particular adsorbent with reference to a particular extract component.

Selectivity of an adsorbent for a particular extract component with reference to a raffinate component may be determined form the ratio of distance between the center of the extract component peak envelope and the tracer peak envelope (or other reference point) to the corresponding distance between the center of the raffinate component peak envelope and the tracer peak envelope.

The rate of exchange of an extract component with the desorbent can generally be characterized by the width of the peak envelopes at half intensity. The narrower the peak width, the faster the desorption rate. The desorption rate can also be characterized by the distance between the center of the tracer peak envelope and the disappearance of an extract component which has just been desorbed. This distance is again the volume of the desorbent pumped during this time interval.

The absorbent selected for the chromatographic separation of succinic acid from the fermentation broth comprising ammonium succinate may be used in the conventional column chromatography with a dense compact bed. In this compact fixed bed chromatography any of the conventional apparatus employed in static bed fluid-solid contacting may be used. In this compact bed chromatography, the adsorbent is alternatively contacted with the feed mixture and desorbent materials. In one embodiment of the invention, adsorbent is employed in the form of a single static bed and the process is only semi-continuous in the sense the feed is applied to the adsorbent only in intervals alternating with raffinate stream and desorbent stream.

In another embodiment of the dense compact fixed bed chromatography a set of two or more static beds may be employed in fixed bed contacting with appropriate valves so that the feed mixture is passed through one or more adsorbent beds while the desorbent materials can be passed through one or more of the other beds in the set. The flow of feed mixture and desorbent materials may be either up or down through the desorbent.

One of the issues associated with single column elution chromatography is that the column material is not utilized efficiently in the separation zone, the section of the column where the components are resolved. The separation zone actually shrinks as the components flow through. One way to overcome this limitation is to sequentially add multiple samples on the top of the column. However, such a sequential addition requires careful timed delay between loading to avoid overlaps with previous samples and provides only a marginal increase in the effective separation zone of the column. Solid phase remains largely under-utilized and the process also requires excessive amount of solvent. These limitations associated with single column elution chromatography can be overcome by using the continuous ion exchange chromatography.

The continuous ion exchange chromatography is more efficient than fixed adsorbent bed system and is preferred embodiments in the practice of the present invention. In the continuous ion exchange chromatography, the adsorption and desorption operations are continuously occurring and as a result there is a continuous use of feed accompanied by a continuous production of extract.

The continuous exchange chromatography can be practiced in several different ways. The continuous ion exchange chromatography suitable for the present invention can be operated in two different modes namely (1) moving port system and (2) moving column system. The moving port system consists of a vertical column subdivided into a number of interlinked compartments and the fluid inlets and outlets of each compartment are controlled by specifically designed rotary master valve. A moving column system comprises multiple chromatography columns mounted on a rotary carousal.

The absorbents to be used in the process of this invention will comprise strongly basic anion exchange resins, weakly basic anion exchange resins, strongly acidic cation exchange resins, and weakly acidic cation exchange resins.

The anion exchange resins suitable for the practice of the present invention possess quaternary ammonium, tertiary amine, or pyridine functionality in a cross-linked polymeric matrix, e.g., divinylbenzene cross-linked acrylic or styrene resins. They are especially suitable when produced in bead form and have a high degree of uniform polymeric porosity and exhibit chemical and physical stability. The resins can be gelular (or "gel-type") or "macroreticular." The list of anionic exchange resins suitable for use in the present invention include Amberlite IRA 400 and 900 series adsorbents, XE 275 (IRA-35), and IRA-68 adsorbents manufactured by Rohm and Haas Company, AG1, AG2, AGMP-1, AG3-X4A and AG4-X4 resins manufactured by BioRad and comparable resins sold by Dow Chemical Company such as Dowex 1, 2, 11, MSA-1 and MSA-2.

The strong cation exchange chromatography material of this invention preferably comprises one or more chromatographic support materials (i.e., stationary phases). Suitable chromatographic support materials include, but are not limited to, alumina, magnesium silicates, silica, glass, controlled pore glass, carbon, porous graphitic carbon, zirconium phosphate, hydroxylapatite, calcium phosphate, magnesium carbonate, and polymers or resins. Suitable polymers or resins include, but are not limited to, hydroxyalkylmethacrylate, polyacrylamine, polymacrylate, poly (hydroxyethylmacrylate), polystyrene, styrenedivinylbenzine copolymers, poly (ethyleneglycoldimethacrylate), poly (vinylalcohol), poly (vinylacetate), and poly (vinylpyridine). Preferable are polymers or resins. More preferable are styrene-divinylbenzine copolymers.

The strong cation exchange chromatographic material of this invention further comprises a plurality of ligands, selected from one or more functional groups suitable for strong ion exchange. These functional groups include but are not limited to sulfonic acid, atkylsulfonic acid, phenylsulfonic acid, alkylphenylsulfonic acid, and salts thereof. Preferred are sulfonic acid functional groups and the salts thereof.

Specific examples of acidic cation exchange polymers or resins that may be used include: AMBERLITE 200, AMBERLITE IR-118H, AMBERLITE IR-120PLUS, AMBERLITE IR-122, AMBERLITE IR-130C, AMBERLITE 16641, AMBERLITE IRP-69, DOWEX 50X1-100, DOWEX 50X2-100, DOWEX 50X2-200, DOWEX 50X2-400, DOWEX 50X4-100, DOWEX 50X4-200, DOWEX 50X4-200R, DOWEX 50X4-400, DOWEX 18880, DOWEX 50X8-100, DOWEX 50X8-200, DOWEX 50X8-400, DIAION 1-3561, DIAION 1-3565, DIAION 1-3570, DIAION 1-3573, DIAION 1-3577, DIAION 1-3581, DUOLITE D 5427, and DUOLITE D 5552, which are available from Sigma-Aldrich, St. Louis Mo., U.S.A.; DIAION HPK25, DIAION PK208, DIAION PK228, DIAION SK1B, DIAION SKIBS, DIAION SK104, DIAION SK112, DIAION SK116, DOWEX HCR-S, DOWEX HCR-W2, DOWEX MSC-1, DOWEX 650C, DOWEX G-26 H, DOWEX 88, DOWEX MONOSPHERE 88, DOWEX MONOSPHERE 99K/320, DOWEX MONOSPHERE 99K/350, DOWEX MONOSPHERE 99Ca/320, DOWEX MONOSPHERE 99Ca/350, DOWEX Marathon C, DOWEX -032, DOWEX -406, DOWEX -437, DUOLITE C-280, and DUOLITE C-291, which are available from Supelco, Inc., Bellefonte, Pa., U.S.A.; AMBERLITE IR-120, AMBERLITE IR-120B, AMBERLITE IR-200C, AMBERLITE CG 6000, DIAION SK-1B, DOWEX XUS 40406.00, DOWEX XUS 43518, and DOWEX C500ES. Preferable are AMBERLITE IR-120, AMBERLITE IR-120B, AMBERLITE IR-200C, DOWEX C500ES, DOWEX XUS 43518, and DOWEX XUS 40406.00. Most preferable is DOWEX XUS 40406.00. LEWATIT™ S100, S109, SP 112, SP120 (manufactured by Bayer), etc. In particular, strongly acidic cation exchange resins having a narrow particle size distribution for industrial chromatography, such as UBK-530, UBK-550 (manufactured by Mitsubishi Chemical Cooperation).

According to the present invention, the adsorbent in the chromatographic column functions in the ion exchange mode. When the adsorbent in the chromatographic column function as an ion exchange resin, the fermentation broth comprising ammonium succinate or any other salt of succinic acid can be used directly without any chemical treatment. The succinic acid salt is subjected to a "salt splitting" reaction on the surface of the adsorbent and the succinic acid released in this process is recovered either in the raffinate stream or in the extract stream depending on the chemical nature of the resin used. Thus according to the present invention, the fermentation broth containing a succinic acid salt is directly applied to the chromatographic column containing ion exchange resin. This is in contrast to the requirement in an ion exclusion chromatography. In the case of ion exclusion chromatography for the separation of succinic acid, the fermentation broth containing a salt of succinic acid is first acidified to precipitate the succinic acid and the resulting succinic acid is separated from the rest of components in the acidified fermentation broth based on the degree of charge repulsion by the adsorbent.

Figure 2:
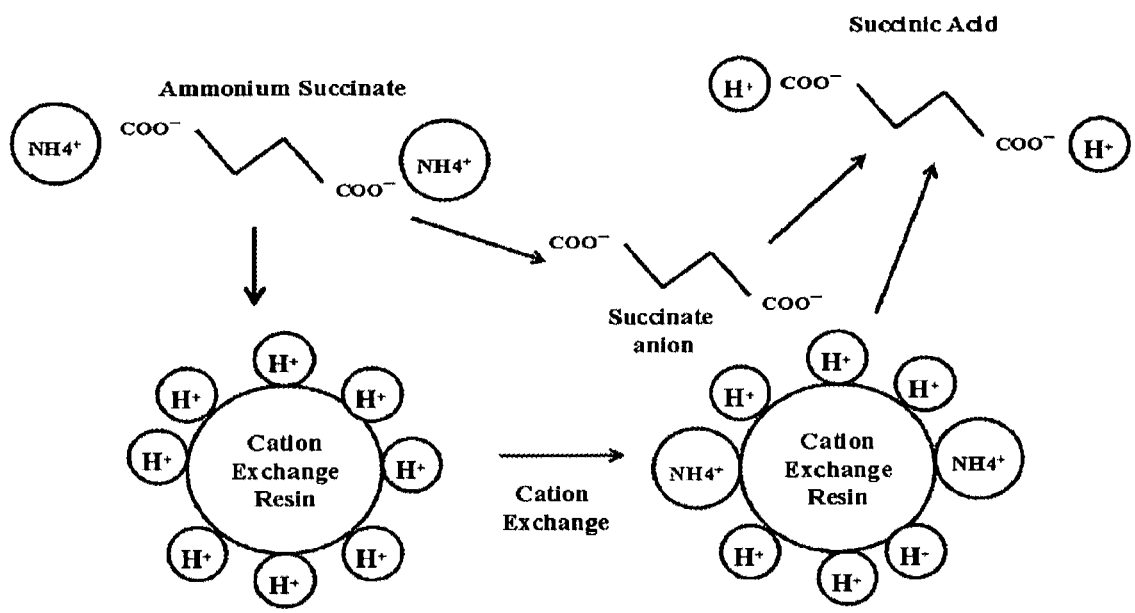
FIG. 2 Diagrammatic representation of cation exchange and conversion of ammonium succinate to succinic acid on the surface of cation ion exchange resin. On the surface of the cation exchange resin, the ammonium succinate is split into succinate anion and ammonium cation. Ammonium cation is exchanged to the proton on the surface of the cation exchange resin with the release of the proton form the cation exchange resin. The proton thus released combines with the succinate anion resulting in the formation of succinic acid.
Figure 3:
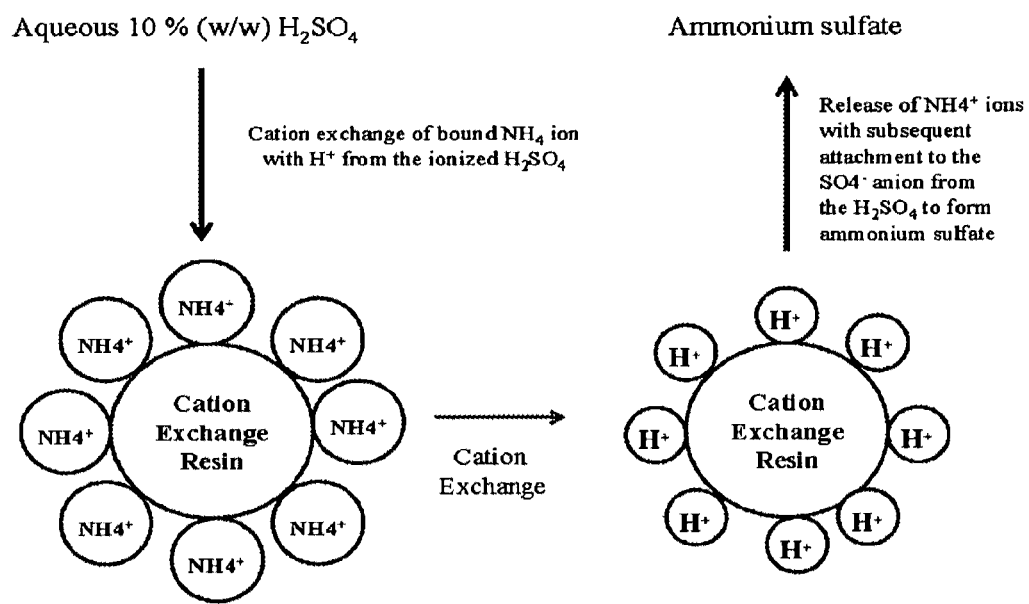
FIG. 3 Diagrammatic representation of regeneration of cation exchange resin with $H_2SO_4$ to produce ammonium sulfate. In the first step of the process for recovering succinic acid from fermentation broth containing ammonium succinate, the fermentation broth is brought into contact with the cation exchange resin. The ammonium succinate is split on the surface of the cation exchange resin and the resulting ammonium cation is exchanged for the proton on the surface of the cation exchange resin. The ammonium bound to the surface of the cation exchange resin surface is released in the second regeneration step using a strong acid such as sulfuric acid. With the sulfuric acid treatment, the ammonium ion in the surface of the resin is exchanged for the proton. The ammonium ion thus released from the surface of the resin combines with the sulfate ion resulting from the dissociation of sulfuric acid leading to the formation of ammonium sulfate.

FIGS. 2 and 3 illustrate the salt splitting reaction on the surface of a cationic ion exchange resin. Ammonium succinate is produced via aqueous phase fermentation, with the goal of producing the succinic acid molecule after separation and purification steps. In the inventive process, the ammonium succinate present in the feed stream is passed over a column of cation exchange resin in the hydrogen form. As the feed stream flows through the column, cation exchange takes place, in which the resin "splits" the ammonium succinate salt, and the released ammonium cation ($NH4^+$) is bound to the resin while the hydrogen ion ($H^+$) initially on the resin, is released into solution. A schematic of this ion exchange reaction is shown in FIG. 2.

Upon release from the cationic ion exchange resin, the hydrogen ion combines with the succinate anion, forming succinic acid. The succinic acid thus produced flows out of the column via a sequence of water rinses, into a chromatographic peak fraction.

In the second step of the "salt splitting" ion exchange chromatography, the bound ammonium cation is released from the resin via passage of dilute sulfuric acid solution. This process regenerates the cationic ion exchange resin for subsequent use. During this regeneration step, the reverse of the first ion exchange step occurs; the hydrogen ion from the fully ionized sulfuric acid solution binds to the resin with simultaneous release of the previously bound ammonium cation. The released ammonium cation then combines with the sulfate anion of the ionized sulfuric acid, yielding ammonium sulfate in solution. By means of doing a sequences of pure water washes, ammonium sulfate is then washed out of the column into its own chromatographic peak fraction. The scheme for the regeneration of the cation exchange resin with production of the ammonium sulfate is illustrated in FIG. 3.

The ability of the adsorbent to carry out the 'salt splitting" reaction on the ammonium succinate molecules present in the fermentation broth is determined by the acid dissociation constant values for adsorbent and ammonium succinate molecule. The acid dissociation constant is also referred as "pKa" and it is related to the equilibrium constant for the dissociation of an acid in aqueous solution into its constituent cation and anion. In one embodiment of the present invention, the aqueous solution comprising ammonium succinate is contacted with an acid ion exchange resin having a pKa value which is at least 0.5 less than the acid dissociation constant of ammonium succinate. The ammonium cation released as a result of "salt splitting" reaction, is bound to the ion exchange resin. The ammonium ion bound to the ion exchange resin can be released by a washing step involving an acid having a pKa value which is at least 0.5 less than the pKa value for the ion exchange resin in its salt form.

In another embodiment of the present invention, an anionic ion exchange resin is used as an adsorbent. In the first stage of the reaction, the succinic anion derived from ammonium succinate is adsorbed to the strong anion exchange resin by the formation of the ionic bonds between the succinic acid molecule and ion exchange sites on the resin. At this stage most of the neutral or cationic material, or large molecules or cellular debris, pass through the resin. In the next stage, the resin is washed with water to remove unbound contaminants that are trapped in the ion exchange resin. Following this wash step, the succinic anion is displaced from the resin by exchanging the adsorbed succinic ion for a stronger inorganic ion. After the removal of the succinic acid from the column, the anion exchange resin is prepared for further cycles of succinic acid adsorption by regenerating the anion exchange sites on the resin. This is accomplished by treating the resin with a strong acid, such as sulfuric acid or hydrochloric acid, which causes the inorganic anion to be exchanged for the succinate anion. The net result of using an anion exchange resin with a fermentation broth containing ammonium succinate is the separation of purified succinic acid.

The succinic acid thus recovered from the fermentation broth through chromatographic procedure can further be purified through nanofiltration.

EXAMPLES

Example 1

Clarification of Fermentation Broth

A membrane suitable for microfiltration (MF) with a pore size of 0.1 μM and another membrane suitable for ultrafiltration (UF) with a cut-off value of 150 kDa were tested for their efficiency in clarifying the fermentation broth comprising ammonium succinate. The characteristic features of these two different membranes are shown in Table 1 below.

Figure 4:
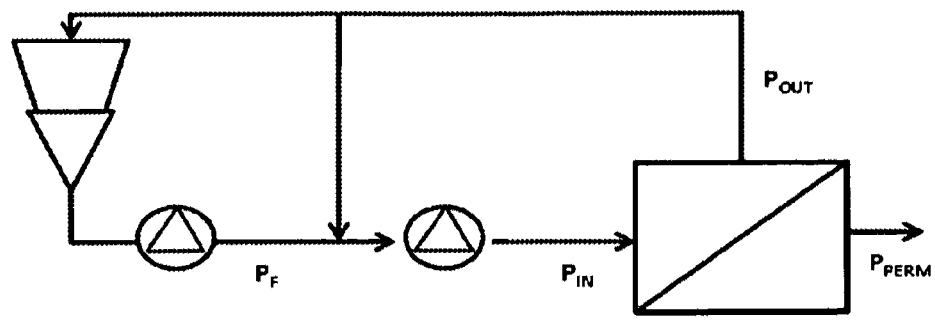
FIG. 4. Scheme for the clarification of fermentation broth containing ammonium succinate. Abbreviations used: $P_F$=Feed pressure; $P_{IN}$=Inlet membrane pressure; $P_{OUT}$=Outlet membrane pressure (close to $P_F$); $P_{PERM}$=Permeate pressure (regulated by a valve opening); $DP=P_{IN}-P_{OUT}$: pressure drop (approximately 1.5 bar); $TMP=(P_{IN}+P_{OUT})/2-P_{PERM}$: Transmembrane pressure.

The clarification pilot scheme with these two membranes is provided in FIG. 4. The permeate flow rate was measured as a function of the trans-membrane pressure (TMP) for each membrane. For this step, the feed broth flows through the membrane and the TMP was varied by opening the permeate circuit. Both retentate and permeate are re-circulated constantly to keep the volumetric concentration factor (VCF) at 1. The permeate obtained with both the membranes were clear although the flow rates were higher with the widest membrane (cut off: 0.1 μM). The membrane with pore diameter of 0.1 μM showed a flow rate of 250 l/h/m$^2$ with TMP=0.8 bars. The other membrane for ultrafiltration with a 150 kDa cut-off showed a flow rate of 300 l/h/m$^2$ with TMP=1.6 bars.

Subsequent clarification of fermentation broth comprising ammonium succinate was performed in batch mode at 35-39° C. using the 150 kDa cut-off membrane to guarantee a good permeate quality and limit the fouling risks. A concentration factor of VCF: 10 was reached at pilot scale at TMP>2 bars with an average flow rate of 143 l/h/m$^2$. The estimated succinate recovery was 87% after clarification at VCF=10. An additional diafiltration helped to increase the succinate recovery rate up to 94%. At industrial scale, it is possible to reach the succinate recovery up to 99% with the following parameters: Free column volume (FCV)=20 and Diafiltration ratio water/retentate=4.5/1 (Table 2).

Example 2

Cationic Ion Exchange Chromatography

In this inventive process, a preparative chromatography column (1.6 cm dia.×100 cm length) containing a strong acid cation exchange resin such as Dowex G-26 H or Lanxess Lewit MonoPlus S 100H was utilized to split the ammonium succinate molecule and provide two (2) hydrogen ions (H$^+$) for every succinate molecule. Lanxess resin 108H can also be used in place of Lanxess resin S 100H. This process yields succinic acid in solution which is then washed out of the column via a sequence of 'slow' and 'fast' pure water rinses.

As the ammonium succinate molecule is split via the strong acid cation exchange resin, the ammonium cation (NH$_4^+$) is bound to the cation exchange resin. After pure water rinses have been conducted to wash out the succinic acid, the resin bed is washed with sulfuric acid in appropriate concentrations to regenerate the cation resin beads. In this step, the hydrogen ion (H$^+$) from the sulfuric acid is exchanged with the previously bound ammonium ion (NH$_4^+$), yielding ammonium sulfate (NH$_4$)$_2$SO$_4$ in solution. The ammonium sulfate is then washed out of the column via a sequence of 'slow' and 'fast' pure water rinses into its own chromatographic peak fraction.

An operating cycle for this process comprises the following steps: (1) Addition of feed at appropriate volume and at appropriate flow rate. The feed can be applied at a volume in the range to 1.0 column volume (CV) to 2.5 CV. In the preferred embodiment, the feed is added in the range of 1.2 CV to 2.2 CV and in the most preferred embodiment, the feed is added in the range of 1.5 CV to 1.7 CV. It should be kept in mind that the volume of the feed to be added is very much dependent on the concentration of ammonium succinate in the feed and the adsorption capacity of the ion exchange resin being used. Based on the concentration of the ammonium succinate present in the fermentation broth and the adsorption capacity of the ion exchange resin being used, the suitable volume of the feed to be added can be calculated so that the entire amount of ammonium succinate present in the feed is split on the surface of the ion exchange resin and there is no problem of saturation of ion exchange resin with ammonium or succinate depending upon the type of ion exchange resin being used and an over flow of ammonium succinate in the raffinate stream. Similarly, the feed flow rate can be in the range of 2 to 4 bed volume per hour (BVH). In a preferred embodiment, the feed flow rate can be in the range of 2.5 to 3.5 BVH and in the most preferred embodiment, the feed flow rate is in the range of 2.9 to 3.2 BVH. (2) A slow rinse step wherein the chromatographic column is washed with 1 to 4 CV of water added at the flow rate of 1 to 4 BVH; (3) A fast rinse step wherein the chromatographic column is washed with 1 to 4 CV of water at the flow rate of 5-10 BVH; in a preferred embodiment, the fast rinse is carried out at the flow rate of 7 to 9 BVH. (4) Regeneration step wherein the column is washed with 1 to 4 CV of a strong acid at appropriate concentration at the flow rate of 1-4 BVH. The strong organic acid suitable for the present invention is selected from a group consisting of hydrochloric acid, nitric acid, sulfuric acid and phosphoric acid. The concentration of the strong acid is selected in such a way so that the ion exchange resin is regenerated fully in a short period of time as evidenced by chromatographic profile. (5) A slow rinse step wherein the column is washed with 1-4 CV of water at the flow rate of 1-4 BVH; and (6) A fast rinse step wherein the column is washed with 6-10 CV of water at the flow rate of 5-10 BVH. These operating conditions are provided only as an example. These operating conditions may be appropriately modified to achieve the maximum recovery of succinic acid with very high level of purity.

Figure 5:
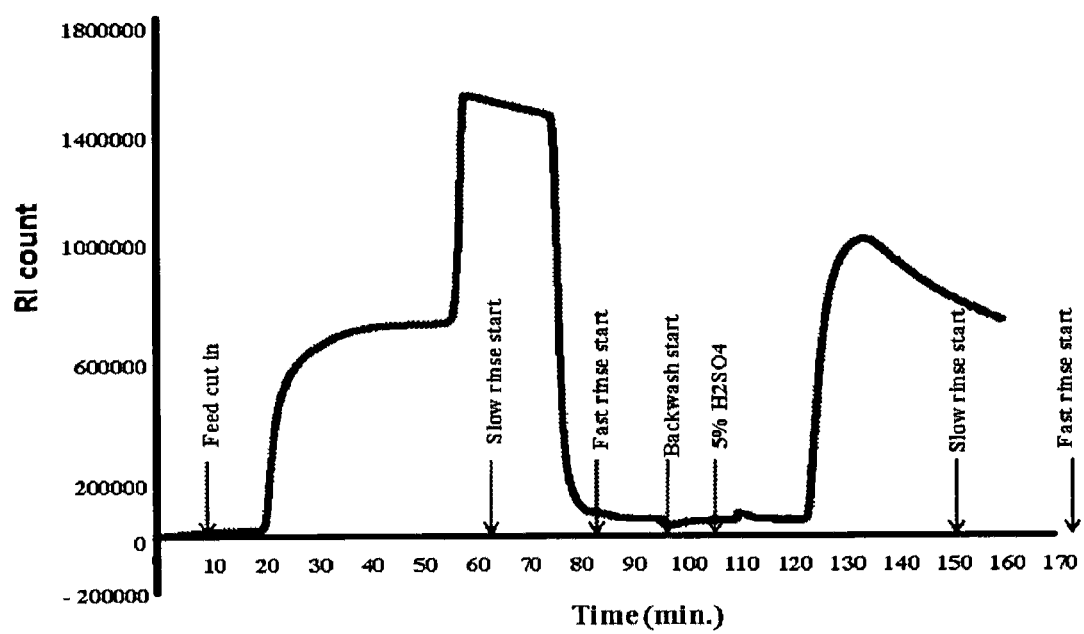
FIG. 5 Chromatographic profile of fermentation broth containing ammonium succinate on a chromatographic column containing Dowex G-26 H resin. Regeneration of cationic ion exchange resin was done with 5% (w/w) $H_2SO4$. The time points for the introduction of feed stream, and the starting point for the slow rinse, the fast rinse, the backwash and sulfuric acid addition are indicated by the downward pointing arrows on the X-axis showing the time in minutes. Shown on the Y-axis is the value for refractive index of the samples coming out of the chromatographic column. Two distinct peaks are seen in the elution profile obtained in this experiment. In the first peak two different sub-peaks could easily be recognized. The first sub-peak which is flat corresponds to the elution of succinic acid. The second sub-peak which is higher than the first sub-peak corresponds to the un-dissociated ammonium succinate fraction coming out of the column. The second peak which is only partially developed in this figure corresponds to the ammonium sulfate fraction.

The fluid coming out of the column containing cation exchange resin was passed through a refractometer (Shimadzu RID-10 with Control Unit CBM-28) to measure the refractive index of the fluid coming out of the chromatographic column (FIG. 5). The fluid line coming out of the refractometer was also passed through an UV Diode array spectrophotometer to monitor the absorbance at 210 nm. Besides these optical measurements on the fluid coming out chromatographic column, chemical analysis was also done on the fractions collected from the chromatographic column. Five different fractions were collected from the chromatographic column during a time course of 305 minutes as shown in Table 3 and in FIG. 7.

The five different fractions collected as described in the Table 3 were analyzed for the content of succinic acid, acetic acid, $SO_4^{2-}$ and $NH_4^+$. Succinic acid and other organic acid impurities present in the fermentation broth were analyzed on Agilent 1200 HPLC apparatus with BioRad Aminex HPX-87H column. BioRad Microguard Cation was used as a guard column. The standards for HPLC analysis were prepared in 0.008N sulfuric acid. The HPLC column temperature was maintained at 50° C. Sulfuric acid at 0.008N concentration was used as a mobile phase at the flow rate of 0.6 ml/min. Quantification of various components was done by measuring their absorption at 210 nm.

Ammonium ion concentration was measured using Mettler Toledo combination $NH_4^+$ ion selective electrode (ISE) with a meter capable of reporting in my. Standard solutions (5000, 500, 50 and 5 ppm ammonium) were prepared by dissolving ammonium sulfate in water. Test samples were prepared by dissolving known quantity of succinic acid crystals in pure water.

Sulfate analysis was performed using the Method 300.0 for the determination of inorganic ions by ion chromatography (Revision 2.1. August 1993) as provided by Environmental Monitoring Systems Laboratory, Office of Research and Development, U. S. Environmental Protection Agency, Cincinnati, Ohio, USA.

Figure 6:
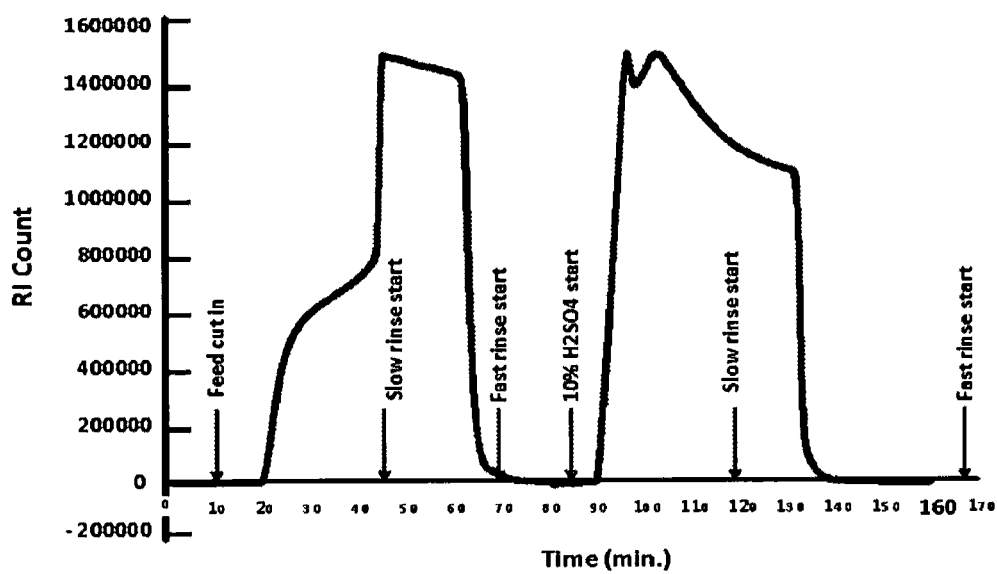
FIG. 6 Chromatographic profile of fermentation broth containing ammonium succinate on a chromatographic column containing Dowex G-26 H resin. Regeneration of cationic ion exchange resin was done with 10% (w/w) $H_2SO4$. The time points for the introduction of feed stream, and the starting point for the slow rinse, the fast rinse, the backwash and sulfuric acid addition are indicated by the downward pointing arrows on the X-axis showing the time in minutes. Shown on the Y-axis is the value for refractive index of the samples coming out of the chromatographic column. The first sub-peak which is flat corresponds to the elution of succinic acid. The second sub-peak which is higher than the first sub-peak corresponds to the un-dissociated ammonium succinate fraction coming out of the column. The second peak which is only fully developed in this figure corresponds to the ammonium sulfate fraction.

Initial development work done with Dowex G-26 H resin was focused on optimizing the concentration of sulfuric acid required to regenerate the Dowex G-26 H resin after the fast rinse with water. FIGS. 5 and 6 show the results from the experiments for optimizing the sulfuric acid requirement for the regeneration of cation exchange resin after an initial salt splitting reaction involving ammonium succinate. These two figures show the profile for the refractive index of the solution coming out of the chromatographic column during the initial 160 minutes in two different experiments. Measurement of succinic acid, acetic acid, $SO4^{2-}$ and glycerol at different time during the operation of chromatography was also made.

A fermentation broth obtained from using KJ122 strain of *E. coli* with an initial ammonium succinic acid concentration of 65 g/L was loaded on the chromatographic column with Dowex G-26 H resin. 2.36 CV of feed was added to the chromatographic column. In the experiments described in FIG. 5, peak succinic acid concentration of 64.69 g/L was observed in the fraction eluting at 60 minutes. At the same time point, the glycerol concentration was found to be 1.67 g/L and the acetic acid concentration was found to be 3.94 g/L in the fraction eluting from the column. However, the refractive value continued to increase till 80 minutes and there was a distinct peak between 60 and 80 minutes. The second peak between 60 and 80 minutes represents the breakthrough peak attributable to the elution of ammonium succinate after the cation exchange resin is fully saturated with ammonium cation derived from the salt splitting reaction during the first 60 minutes. As defined in the present invention, the term "breakthrough peak" corresponds to the fraction eluted from the column after the ion exchange resin is saturated with the sulfate ion. In other words, the breakthrough peak essentially contains the original component of the feed solution. In the fraction eluting from the column at 64 minutes, the sulfate concentration was found to be 167.7 ppm and in the fraction eluting at 77 minutes sulfate was not detectable. In the fraction eluting at 85 minutes, the succinic acid concentration was 0.44 g/L and the succinic acid concentration decreased to the level of 0.11 g/L. This observation indicated that by means of optimizing the appropriate feed concentration, it is possible to eliminate the second peak attributable to the excess amount of ammonium succinate in the feed material.

We observed the similar chromatographic profile in the experiment described in the FIG. 6. Two different peak are detectable within the first 80 minutes of the separation. The first peak is attributable to the elution of succinic acid as evidenced by presence of high concentration of succinic acid in the fraction at earlier time points. The succinic acid concentration was found to be 72.45 g/L in the fraction eluted at 45 minute which decreased to the level of 66.12 g/L in the fraction eluted at 55 minutes and to the level of 0.55 g/L at 72 minutes. In the fraction eluting at 92 minute, the succinic acid concentration was found to be 0.07 g/L. In the fraction eluting at 45 minutes, the sulfate concentration was found to be 810 ppm which decreased to the level of 18.2 ppm in the fraction eluting at 72 minutes. These observations taken together suggest that in the experiments reported both in FIG. 5 and FIG. 6, the second peak is attributable to the elution of ammonium sulfate which was not subjected to salt splitting reaction on the surface of the cation ion exchange resin due to the saturation of cation ion exchange resin with the sulfate ion derived from the splitting of the ammonium succinate.

In the experiment shown in FIG. 5, as a way of regenerating the cation exchange resin, 2 CV of 5% (w/w) sulfuric acid was added at 110 minutes to start the regeneration process. This regeneration process is expected to release ammonium sulfate as evidenced by an increase in the refractive index of the fluid coming out of the chromatographic column subsequent to the addition of sulfuric acid. As indicated by the refractive index at 160 minutes, the release of the ammonium sulfate was not complete at 160 minutes with washing done with 5% sulfuric acid. In the fraction eluting at 150 minutes, the sulfate concentration was found to be 9585 ppm. However, as shown in FIG. 6, by increasing the sulfuric acid concentration to 10%, it is possible to achieve the complete regeneration of the cation exchange resin as evidenced by the refractive index value reaching base level. With the use of 10% (w/w) sulfuric acid for regeneration of the cation ion exchange resin, the sulfate concentration in the fraction eluting at 92 minutes was found to be 20128 ppm. The sulfate concentration in the fraction eluting at 139 minute was found to be 2664 ppm and at 221 minute, the sulfate concentration decreased to the level of 36.6 ppm.

Figure 7:
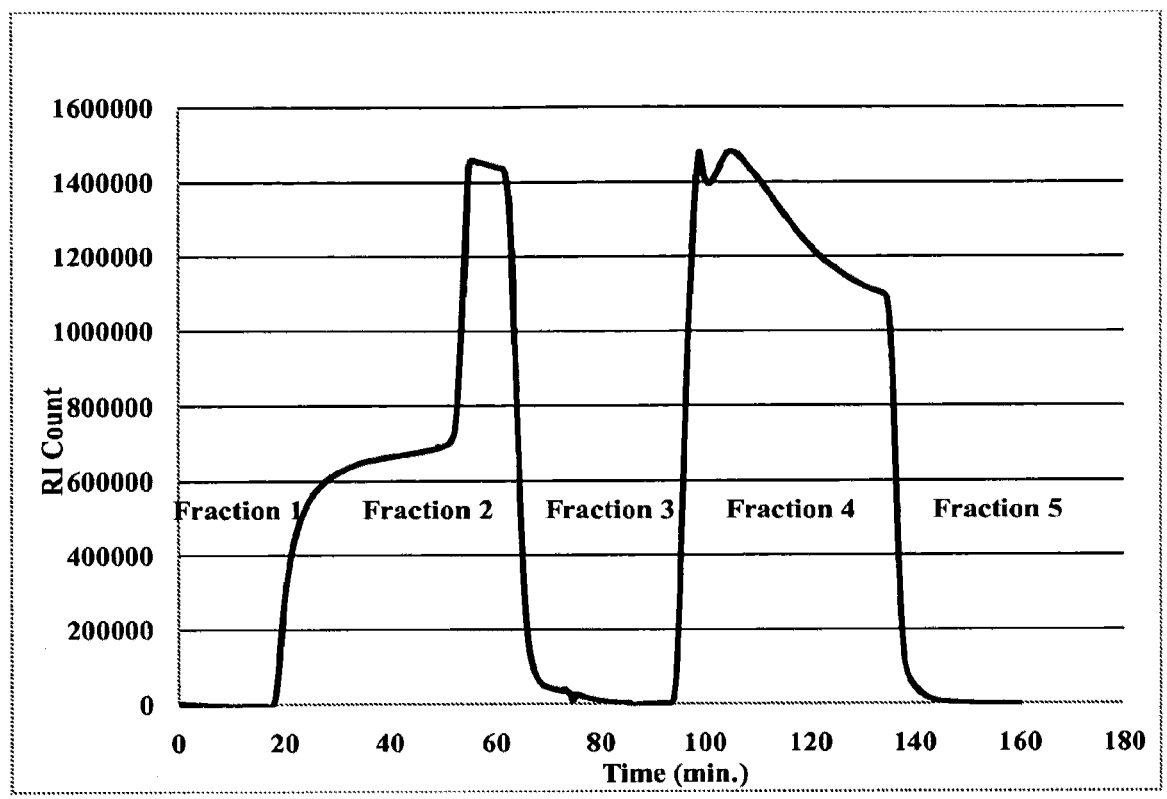
FIG. 7 Chromatographic profile of fermentation broth containing ammonium succinate on a chromatographic column containing Dowex G-26 H resin. Regeneration of cationic ion exchange resin was done with 10% (w/w) $H_2SO4$. Shown in the figure are the portions of the chromatogram corresponding to five different chromatographic fractions collected for subsequent analysis.

After determining that 10% sulfuric acid concentration was optimal for achieving complete regeneration of cation exchange resin, seven more experiments (Experiments 4-10) were conducted using Dowex G-26 H resin. The profile for the refractive index for one of these seven experiments is shown in FIG. 7. The FIG. 7 also shows the regions of the refractive index profile corresponding to various fractions collected. Table 4 provides the purity and the percent recovery of succinic acid in the fraction F2 of the experiments 4-10 done with Dowex G-26H resin.

After optimizing the sulfuric acid concentration required for regenerating a cation exchange resin, experiments were conducted with another cation exchange resin Lanxess S100 H to optimize the feed volume for achieving separation of succinic acid peak from the breakthrough peak. As shown in Table 5, six different experiments were conducted using different volume of feed materials in the range of 1.5 to 2.16 CV.

Figure 8:
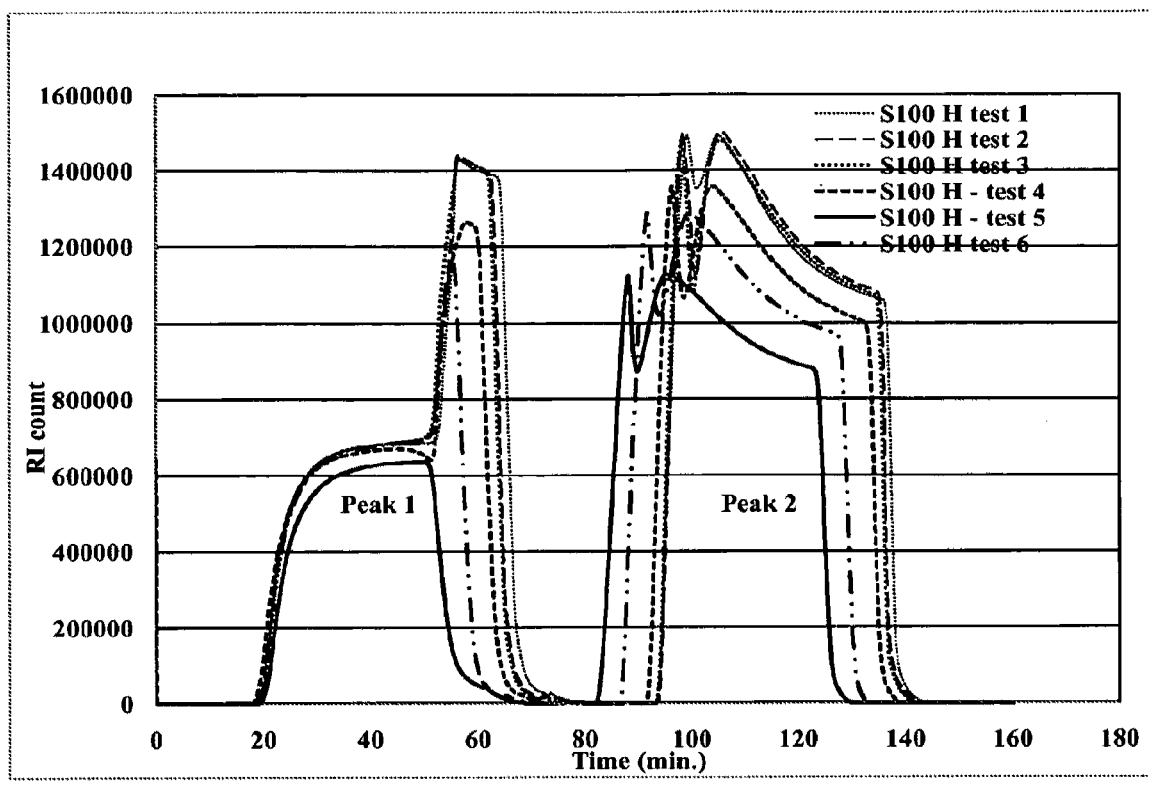
FIG. 8 Multiple Chromatographic profile of fermentation broth containing ammonium succinate on a chromatographic column containing Lanxess S100 H cation resin. Regeneration of cationic ion exchange resin was done with 10% (w/w) $H_2SO4$. Six different chromatographic profiles were obtained from experiments 1, 2, 3, 4, 5, and 6 using different feed volumes as shown in Table 5. Slow rinse and fast rinse were done with 1 column volume of deionized water. Two column volumes of 10% (w/w) sulfuric acid was used to regenerate the resin followed by the addition of 3 column volumes of deionized water in the slow rinse mode and 6 column volumes of deionized water in the fast rinse mode.
Figure 9:
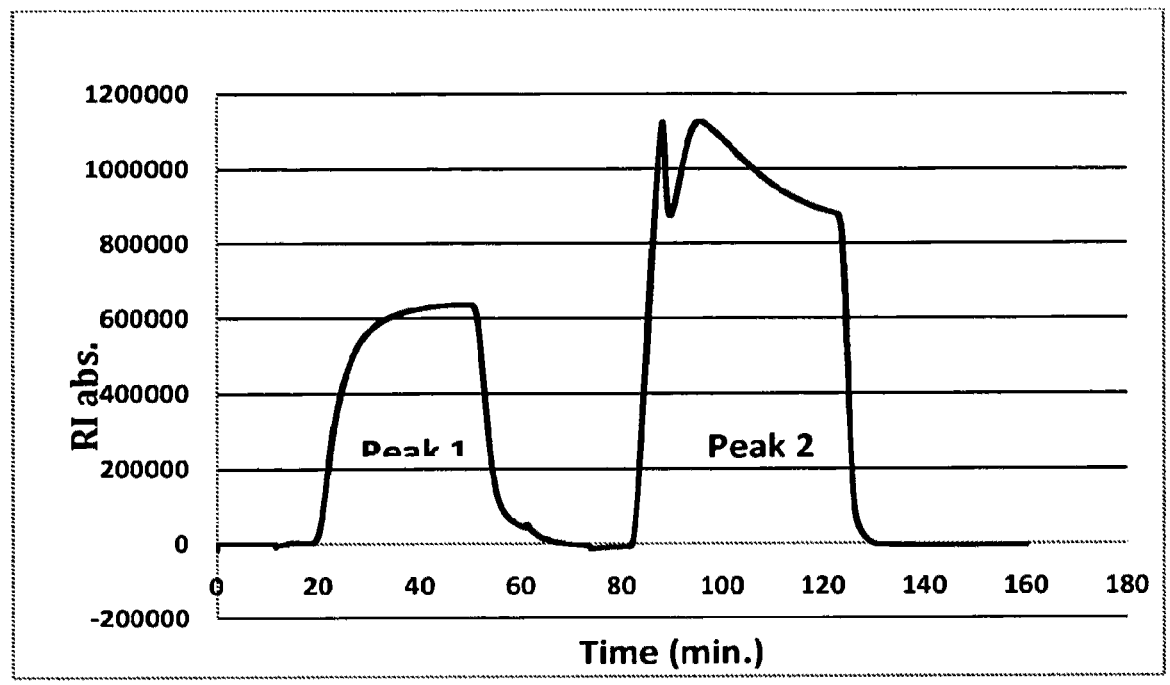
FIG. 9 Chromatographic profile of fermentation broth containing ammonium succinate on a chromatographic column containing Lanxess S100 H cation resin. Regeneration of cationic ion exchange resin was done with 10% (w/w) $H_2SO4$. A 1.5 column volume of feed was loaded onto the column. Slow rinse and fast rinse were done with 1 column volume of deionized water. Two column volumes of 10% (w/w) sulfuric acid was used to regenerate the resin followed by the addition of 3 column volumes of fluid in the slow rinse mode and 6 column volumes of deionized water in the fast rinse mode.

The refractive index profiles for these six different experiments are shown in the FIG. 8. As shown in FIG. 8, by lowering the feed volume to 1.5 CV, it is possible to eliminate the breakthrough peak and achieve succinic acid recovery in a distinct single peak. For clarity, FIG. 9 shows the profile of the refractive index only for Test 5 done with Lanxess S100 H cation exchange resin using 1.5 CV of feed. Table 6 provides the result on the quantitative analysis of succinic acid, acetic acid, $SO_4^{2-}$ and $NH_4^+$ content in the Peak 1 and Peak 2 fractions shown in FIG. 8. As the results shown in FIG. 8 and Table 6 indicate, by means of controlling the feed volume, it is possible to eliminate the breakthrough peak and achieve succinic acid recovery in a single peak. This is evidenced by the fact that in the Test 5, with 1.5 CV of feed addition, it was possible to recover succinic acid in a single peak. This peak showed a minimal value for $NH4^+$. The amount of $NH4^+$ in the Peak 1 fraction of Test 5 was 100 times lower than the $NH_4^+$ content in the Peak 1 fraction from the other tests where higher volume of the feed was used. In addition the $SO4^{2-}$ value for Peak 1 fraction was lower in all the tests suggesting that the rinsing protocol used in these experiments was optimal to get rid of all the impurities before priming the column with next round of feed addition.

Example 3

Pulse Test Results For Chromatography With Anion Exchange Resin

In order to select an anion exchange resin to be used in the continuous ion exchange chromatography pulse test was conducted with fermentation broth and three different anion exchange resins. The fermentation broth had the composition as shown in the Table 7.

The chemical characteristics of three different anion exchange resins tested in this invention are provided in Table 8. The sample elution sequential profile with each of these three anion exchange resin is provided in the Table 9. The columns (initially under sulfate form are overloaded with the raw broth with the volume provided in the Table 9 to estimate the maximum resin capacity. The column was rinsed with water followed by a regeneration step involving washing with 10% sulfuric acid and a rinse with water. The performance summary for each of three resins tested in the present invention is provided in Table 10. Resin XA 3121 showed poor efficiency regarding succinate capacity. During the first cycle resins XA 4122 and XA 3114 gave very close results either for the total exchange capacity or the rinse volume needed.

After reviewing the results from pulse tests with three different anion exchange resins, XA 3114 was chosen for the continuous ion-exchange trials. This selection of XA 3114 resin for continuous ion-exchange operation was based on two reasoning: (1) At the industrial scale, the regeneration rate is limited to minimize the chemicals consumption. In order to stay under acceptable leakage values for succinate into the raffinate, one could lower the working capacity of the resins compared to the maximum capacity measured at laboratory scale. Thus, one can reach more ion exchange capacity with the XA 3114 which has more capacity than the XA 4122. (2) The XA 3114 is a monosphere type resin which helps to increase the separation efficiency and minimize the rinse water volumes.

Example 4

Continuous Ion Exchange Chromatography With Anion Exchange Resin

Figure 10:
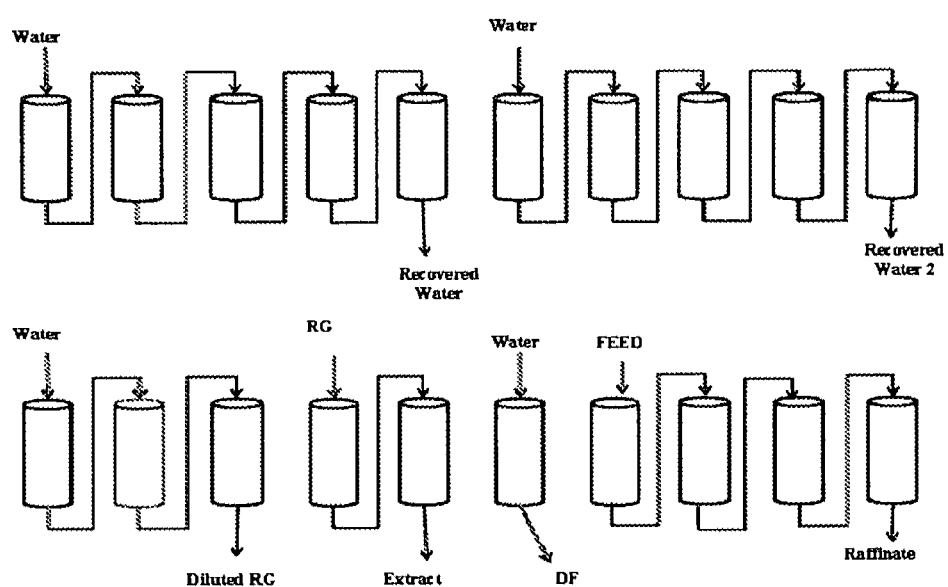
FIG. 10 Modules for continuous ion exchange chromatography with anionic ion exchange resin for the separation of succinic acid from the fermentation broth containing ammonium succinate. The continuous ion-exchange sequence is performed on ten columns filed with anionic resin (0.4 L each). The pilot was divided in 4 areas, each composed of 1 to 3 columns. Each sequence is divided in 2 steps as shown in the figure. Succinate is caught on the anionic resin and released during acid regeneration. Regeneration was performed in co-current mode. Ammonium sulfate is recovered in the raffinate and succinic acid in the extract. The continuous ion-exchange process is performed at 50° C. during the trial to avoid any crystallization of succinic acid into the ion-exchange columns.

Compared to the batch mode, continuous ion-exchange allows for an increase in the purity of the succinic acid fraction, decrease the overall chemical composition and a decrease in the water consumption. The continuous ion-exchange chromatography was performed on ten columns filled with anionic resin (0.4 L/column). The pilot was divided in 4 areas, each composed of 1 to 3 columns. Each sequence was divided in 2 steps as shown in FIG. 10. Succinate was caught on the anionic resin and released during the acid regeneration. Regeneration was performed in co-current mode. Ammonium sulfate was recovered in the raffinate and succinic acid in the extract.

The continuous ion-exchange process was performed at 50° C. during the trials to avoid any crystallization of succinic acid into the ion-exchange columns.

On a regular basis inlets and outlets were displaced downstream from one column to the next one to simulate a counter-current displacement of the resin. For example, on FIG. 10, at the end of the step, column n°1 becomes column n°4 for the nest sequence.

Six different trials corresponding to six different settings were performed to reach both recovery and purity goals. The volume of injected product and the concentration of the feed and regenerant differed for each setting. Table 11 provides the sequential description for continuous ion-exchange using an anion resin.

For settings 1 to 3, the outlet of regeneration was cut in two parts: the first part is collected as extract product while end of collect was sent to the dilute regenerant (DRG) stream. For settings 4 to 6, the whole outlet regeneration was collected as extract product.

Regenerant concentration was fixed at 80 g/L $H_2SO_4$ in order to avoid a too high succinic acid concentration into the extract fraction which could lead to acid crystallization into the column. In addition, the columns were thermostated at 50° C.

The compositions of the different flows corresponding to each of the previous settings are reported in Table 12.

For setting 1 to 5, the feed succinate concentration was 55-60 g/L. From setting 6, the feed product was diluted to 50 g/L succinate in order to improve the exchange with sulfate on the anionic resin and reduce the succinate loss to the raffinate. This last setting produced 80 g/L ammonium sulfate in the raffinate, with 2.8 g/L leakage of succinate. The extract concentrated at 41 g/L succinic acid and was contaminated with little amount of other anions (under 1 g/L sulfate).

The dilute feed concentration was 2 g/L in ammonium succinate but contained 3 g/L of sulfate anions. This can be used as dia-filtration water in the clarification step.

In the dilute regenerant, the sulfate concentration reached 35 g/L. It can be used directly as a solvent to prepare the regenerant again. It contained approximately 2 g/L succinate which is then recycled to the columns and not lost. Mass balances are generally equilibrated and did confirm the results. The mass balance was more difficult to establish for acetate which was less concentrated. Table 13 summarizes the performances calculated for each setting.

It is to be noted that the succinic loading and recovery rates would be higher by working with the resin under chloride form, and regenerating with HCl instead of $H_2SO_4$. Indeed, the competition is high on the resin between succinate and sulfate, which are both divalent. This results in a higher succinate leakage into the raffinate since the exchange between the two species is more difficult in production mode. On the other hand, the competition between succinate and chloride turns in favor of succinate since the resin has more affinity for divalent species than for monovalent ones. Consequently, regenerating the resins with HCl would result in a lower succinate leakage to the raffinate and a high recovery rate. In addition, $H_2SO_4$ is considered as a non-completely dissociated acid which means that the resin requires a higher $H_2SO_4$ regeneration rate than with HCl which is completely dissociated to reach the same regeneration efficiency.

Example 5

Polishing Trials

The aim of the polishing trials was to determine the necessary design to ensure an excellent succinic acid crystal quality. This step involves the use of nanofiltration (NF) and the ultimate objective of the polishing procedure was to obtain 99.5% pure white crystals of succinic acid. The ion exchange extract was treated by NF to remove the color before sending the product to the crystallization step. The NF permeate (decolorized succinic acid) was sent to the crystallization step. The characteristics of the filter used in the nanofiltration are provided in the Table 15.

Figure 11:
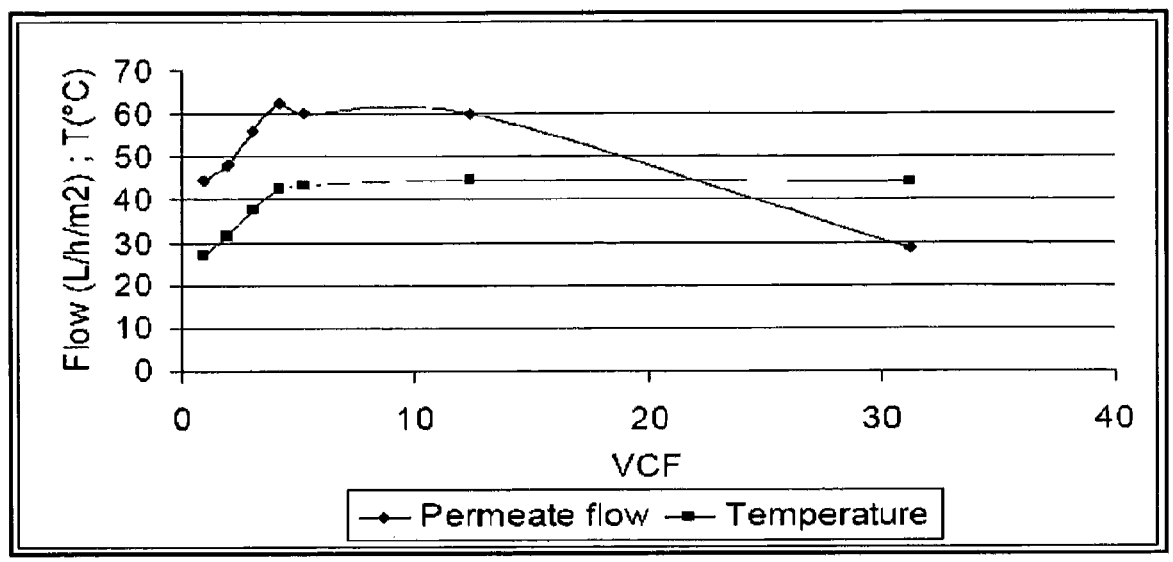
FIG. 11 Permeate flow rate for nanofiltration process with succinic acid recovered from the fermentation broth containing ammonium succinate. Shown in the X-axis is the volumetric concentration factor and on the Y-axis are the flow rate in $L/m^2/hr$ and temperature.

The Feed product from ion exchange extract setting 6 was used as the raw material during the polishing trials. When FCV=31 was reached the experiment was stopped because of a low retentate levels. Two final dia-filtrations (ratio water/retentate=1/1 each) were performed to increase the succinate recovery rate. The permeate flow evolution is reported in FIG. 11. As shown in FIG. 11, the polishing trial presented an unusual behavior. The flow rate showed an increase in the flow rate before showing the standard decreasing tendency. This could be explained by both effects of the temperature increase which occurred in parallel and at relatively constant retentate composition.

Effluent composition is provided in Table 16. As measured by the optical density at 420 nm, there was a 86% optical density reduction between the feed and the permeate resulting from nanofiltration.

As expected, most of the succinic acid is recovered in the permeate. Estimated retention rates and permeate fractions representing the fraction of the feed content which is recovered into the permeate are indicated in Table 17

Weak organic acids (succinate and lactate) mostly under their associated acid form reside at a pH of 2.5. Consequently, they are mostly not ionized and their water salvation number is low. As small molecules they can easily pass through the NF membrane to the permeate stream: their retention rate is low (or even negative for lactate). Operating at VCF=31 allows to recover 96% of the succinic acid. Additional dia-filtration helps to reach 98% recovery. This rate can be improved again easily.

Salts (sulfate and ammonium) are more solvated under the ionic form and then occupy a larger volume especially the divalent sulfate anions. Moreover, sulfate and ammonium stay coupled to respect electroneutrality of the solution. Both of their retention rates are high.

Example 6

Evaporation And Crystallization of Succinic Acid

The succinic acid recovered from the continuous ion exchange chromatography is evaporated to reach an adequate succinic acid concentration to start the crystallization step. Succinic acid has a boiling point of 253° C. while the other potential organic acid contaminants in the succinic acid preparation such as acetic acid and lactic acid have a lower boiling point. The boiling point of acetic acid is 118° C. and the boiling point of lactic acid is 122° C. Thus using an evaporation step, the succinic acid was concentrated up to 420 g/L besides removing some of the acetic acid and lactic acid contaminations.

Figure 12:
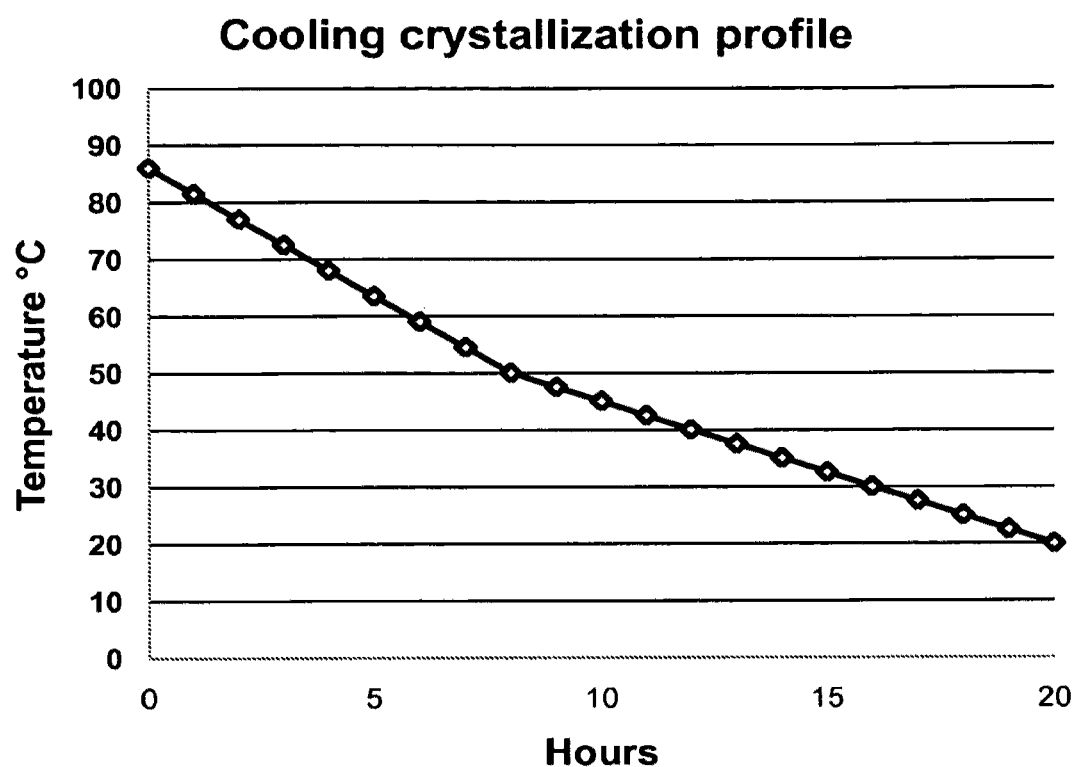
FIG. 12 Cooling profile for the crystallization of succinic acid obtained from fermentation broth containing ammonium succinate. Succinic acid was concentrated up to 420 g/L at 85° C. The crystallization was initiated with pure succinic acid crystals seeds (80 μm). Temperature transition from 85° C. to 20° C. was achieved in 20 hours.

The concentrated succinic acid was crystallized by cooling the vessel. The following protocol was used for crystallization: (1) Concentrating succinic acid up to 420 g/L at 85° C. (2) Initiating the crystallization with pure succinic acid crystal seeds of 80 μm diameter. (3) Cooling the product from 85° C. to 20° C. along 20 hours according to the profile shown in FIG. 12. (4) Washing the final crystals with a saturated pure succinic acid solution.

Crystallization procedure was carried out with the following three different preparations of succinic acid. (1) Non-polished extract from continuous ion exchange chromatography (2) NF-polished extract from continuous ion exchange chromatography (3) A synthetic succinic acid preparation containing 25 g/L of sulfate anions. Table 18 provides the results of the crystallization experiment done with these three different preparation of succinic acid. As the results shown in Table 20 indicate, more than 99.85% crystal purity was reached for each of the three samples tested. The crystallization yield ranged from 895 to 93%.

Figure 13:
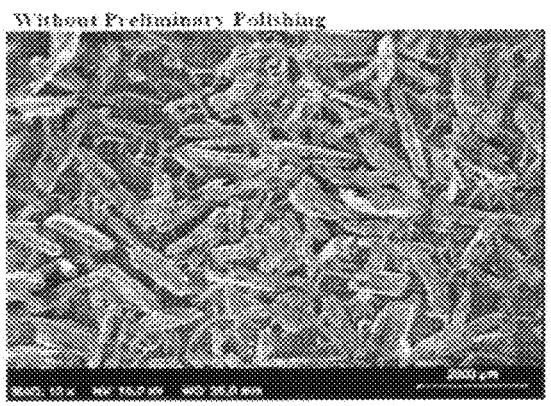
FIG. 13 Scanning electron micrographs of succinic acid crystals obtained from continuous ion exchange chromatographic equipment with anionic ion exchange resin. Shown on the left is the scanning electron micrograph of the crystals obtained without the polishing step involving nanofiltration. Shown on the right side of the figure is the scanning electron micrograph of the crystals obtained after polishing step involving nanofiltration.
Figure 13:
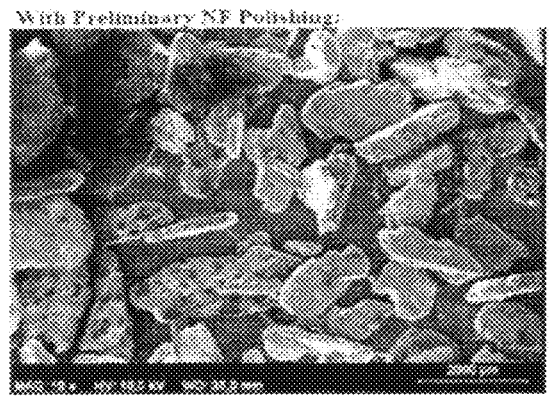

Color of the crystalline succinic acid was determined by measuring the optical density of filtered 100 g/L solution of the final product (Table 19). Succinic acid crystals resulting from the non-polished extract of ion exchange chromatography were brown in color. The crystals were needle shaped with the length of 1-2 mm. As shown in the scanning electron micrographs in FIG. 13, the NF polished crystals were white and were bigger in size when compared to the crystal from non-polished extract.

Example 7

Crystallization of Ammonium Sulfate Effluent

A mix of raffinate produced with settings 2-4 was used as a raw material for the salt effluents crystallization trials. Raffinate was concentrated to 50× before starting the crystallization at 95° C. by constant evaporation. The concentration of raffinate was performed in two steps. In the first step, a reverse osmosis was used to concentrate the raffinate from 80 g/L. ammonium sulfate concentration to 160 g/L ammonium sulfate concentration. In the second step, further concentration was achieved by means of evaporation.

Figure 14:
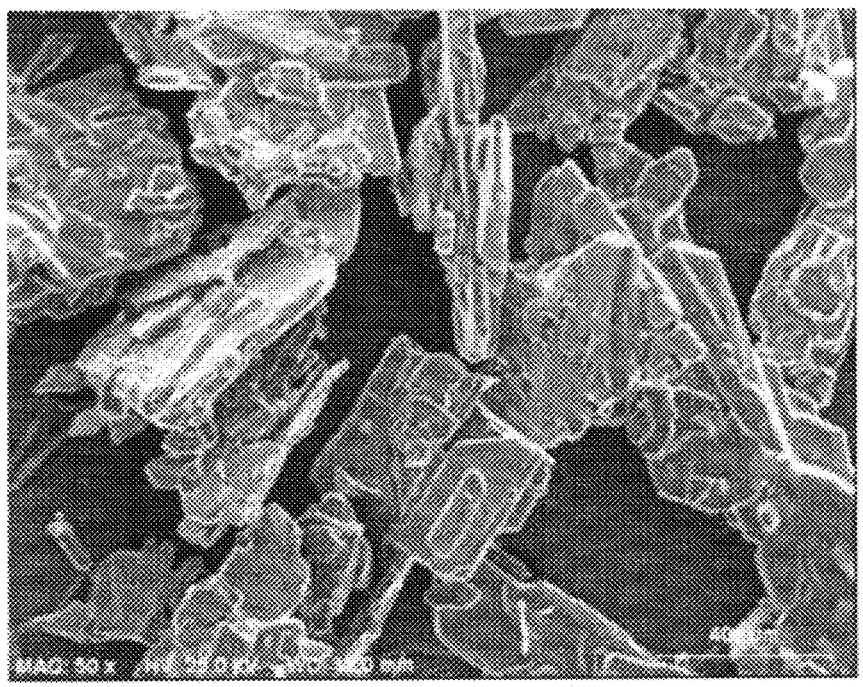
FIG. 14 Scanning electron micrographs of ammonium sulfate crystals recovered from the ion exchange chromatographic process involving fermentation broth containing ammonium succinate.

Table 20 summarizes the composition of the ammonium sulfate crystals obtained from the raffinate produced with setting 2-4 of the continuous ion exchange chromatography. No organic salts were detectable in the crystals. The crystals were brown in color and had distinct shape as shown in the scanning electron micrograph in FIG. 14.

TABLE 1

UF/MF Membrane characteristics

| Type | Cut-off | Linear Speed m/s | Exchange Surface Area m2 | Temperature °C. | Pressure bars |
|---|---|---|---|---|---|
| MF | 0.1 µM DIAM | 5 | 0.25/mb | 35-38 | 1.5 - 3 |
| UF | 150 kDa | 5 | 0.25/mb | 35-38 | 1.5 - 3 |

TABLE 2

Summary of clarification result

| | Volumetric Concentration Factor (VCF) | Diafiltration rate Water/Retentate | Clarification rate % | Succinate recovery rate % | TMP bars |
|---|---|---|---|---|---|
| Lab results | 10 | 0/1 | 93 | 87 | >2 bars |
| Lab results | 10 | 1/1 | 93 | 94 | >2 bars |
| Estimated Industrial | 20 | 4.5/1 | 93 | 99 | >2 bars |

TABLE 3

Fractions collected from chromatographic column

| Fraction No. | Start time (min) | Stop time (min) | Purpose |
|---|---|---|---|
| F1 | 0 | 18 | To measure the carryover $SO_4^{2-}$ and $NH_4^+$ ions from previous cycle |
| F2 | 18 | 70 | To monitor succinic acid recovery |
| F3 | 70 | 94 | To measure spillover of organic acids, $SO_4^{2-}$ and $NH_4^+$ from Fraction F2 |
| F4 | 94 | 141 | To recover ammonium sulfate fraction |
| F5 | 141 | 305 | To measure the level of $SO_4^{2-}$ and $NH_4^+$ ions after final rinse step |

TABLE 4

Purity and recovery of succinic acid in F2 fraction from Dowex G-26 H resin

| | wt. % | | % recovery | |
|---|---|---|---|---|
| | Succinic Acid | Acetic Acid | Succinic Acid | Acetic Acid |
| Test 4 | 93.1 | 4.9 | 90.2 | 79.7 |
| Test 5 | 92.95 | 5.02 | 87.9 | 80.1 |
| Test 6 | 92.8 | 5.06 | 91.9 | 84.7 |
| Test 7 | 92.6 | 5.05 | 94.9 | 87.5 |
| Test 8 | 94.2 | 4.6 | 88.3 | 84.0 |
| Test 9 | 94.2 | 4.6 | 98.5 | 81.3 |
| Test 10 | 94.1 | 4.7 | 94.6 | 79.1 |

TABLE 5

Operating conditions for the column chromatography with Lanxess S100 H cation exchange resin.

| Test # | Feed CVs loaded | CVs for slow rinse | CVs for fast rinse | CVs of 10% $H_2SO_4$ for regeneration step | CVs for slow rinse | CVs for fast rinse |
|---|---|---|---|---|---|---|
| 1 | 2.16 | 1 | 1 | 2 | 3 | 6 |
| 2 | 2.10 | 1 | 1 | 2 | 3 | 6 |
| 3 | 2.09 | 1 | 1 | 2 | 3 | 6 |
| 4 | 2.0 | 1 | 1 | 2 | 3 | 6 |
| 5 | 1.5 | 1 | 1 | 2 | 3 | 6 |
| 6 | 1.75 | 1 | 1 | 2 | 3 | 6 |

TABLE 6

Succinic acid and acetic acid concentrations in the F2 fraction and $NH_4^+$ and $SO_4^{2-}$ concentrations in the Peak 1 and Peak 2 fractions from the chromatography with Lanxess S100 H cation exchange resin.

| | wt. % | | % recovery | | ppm | ppm |
|---|---|---|---|---|---|---|
| | Succinic Acid | Acetic Acid | Succinic Acid | Acetic Acid | $NH_4^+$ in peak 1/peak 2 | $SO_4^{2-}$ in peak 1/peak 2 |
| Test 1 | 93.0 | 5.22 | 93.4 | 88.61 | 4531/15714 | 18/80730 |
| Test 2 | 92.9 | 5.23 | 96.2 | 91.53 | 4146/16904 | 25/89771 |
| Test 3 | 93.1 | 5.44 | 86.6 | 85.57 | 4303/16532 | 11/80601 |
| Test 4 | 92.2 | 5.23 | 98.2 | 91.53 | 3099/15983 | 27/87628 |
| Test 5 | 93.0 | 5.44 | 98.0 | 85.57 | 33/13550 | 19/80177 |
| Test 6 | 91.1 | 5.23 | 99.0 | 91.53 | 1339/17289 | 32/96158 |

TABLE 7

Composition of fermentation broth used in chromatography using anion exchange resin

| Property/Component | Units | Amount |
|---|---|---|
| Brix | 1 gram of sucrose in 100 grams of a solution. | 13.1 |
| pH | | 7.62 |
| Conductivity | [mS/cm] | 83 |
| Succinate | g/L | 55.2–61.9 |
| Acetate | g/L | 4.2–10.9 |
| SO4 | g/L | 0.24 |
| PO4 | g/L | 2.8 |
| Citrate | g/L | 0.6 |
| NH4 | g/L | 27.7–32.6 |
| Na | g/L | 0.07 |
| K | g/L | 5 |

TABLE 8

Resin characteristics

| Resin | Structure | Type | Capacity (eq/L) | Volume (ml) |
|---|---|---|---|---|
| XA 4122/$SO_4^{2-}$ | Acrylic DVB – Quaternary amine | Strong Basic Anion (SBA) Gel Type | 1.25 | 14.92 |
| XA 3114/45/SO4 $^{2-}$ | Acrylic DVB – Tertiary amine | Weak basic Anion (WBA) Gel Type | 1.6 | 14.92 |
| XA 3121/$SO_4^{2-}$ | Acrylic DVB | Weak basic Anion (WBA) Gel type | 2.48 | 14.92 |

TABLE 9

Sample elution sequential

| Step | Effluent | XA 4122 | XA 3114 | XA 3121 | Flow rate | Comments |
|---|---|---|---|---|---|---|
| Production | Ammonium succinate | 3 BV | 4.5 BV | 8 BV | 2 BVH | Down flow |
|  | Water | 3 BV | 3 BV | 4 BV | 2 BVH | Down flow |
| Regeneration | H2SO4 (10%) | 3 BV | 3 BV | 5 BV | 2 BVH | Down flow |
|  | Water | 3 BV | 3 BV | 4 BV | 2 BVH | Down flow |

TABLE 10

Comparison of resins for succinate capture

|  |  | XA 4122 | XA 3114 | XA 3121 |
|---|---|---|---|---|
| Loading | eq/L | 3.1 | 4.7 | 8.8 |
| Capacity | eq/L | 1.4 | 1.4 | 1.02 |
| Theoretical capacity | eq/L | 1.25 | 1.60 | 2.48 |
| Water needed for product rinse | BV (Bed volume) | 1.3 | 1.3 | 1.3 |
| Water needed for regeneration rinse | BV | 2.7 | 2.7 | 2.8 |

TABLE 11

Sequential description for continuous ion-exchange

|  |  | Setting 1 | Setting 2 | Setting 3 | Setting 4 | Setting 5 | Setting 6 |
|---|---|---|---|---|---|---|---|
| Production | Columns/Area | 3 | 3 | 4 | 4 | 4 | 4 |
| Sweetening off | Columns/area | 1 | 1 | 1 | 1 | 1 | 1 |
| Regeneration | Columns/area | 2 | 2 | 2 | 2 | 2 | 2 |
| Rinse | Columns/area | 3 | 3 | 3 | 2 | 2 | 2 |
| Temperature | °C. | 50 | 50 | 50 | 50 | 50 | 50 |
| Product in | BV | 1 | 1 | 0.95 | 0.9 | 0.9 | 1.1 |
| Product out (Raffinate) | BV | 1 | 1 | 0.95 | 0.9 | 0.9 | 1.1 |
| Water for sweetening off | BV | 0.95 | 0.75 | 0.65 | 0.4 | 0.4 | 0.4 |
| Dilute feed (DF) | BV | 0.95 | 0.76 | 0.65 | 0.4 | 0.4 | 0.4 |
| Regeneration H2SO4 80 g/L | BV | 1.5 | 1.5 | 1.2 | 1.2 | 1.2 | 1.2 |
| Regenerant effluents (extract) | BV | 1.2 | 1.3 | 1.1 | 1.2 | 1.2 | .12 |
| Dilute Regenerant (DRG) | BV | 1.15 | 1.05 | 0.95 | 0.85 | 1.1 | 1.1 |
| Rinse regeneration | BV | 0.85 | 0.85 | 0.85 | 0.85 | 1.1 | 1.1 |
| Loop (RW1) | BV | 0.35 | 0.65 | 0.65 | 0.65 | 0.65 | 0.65 |
| Loop (RW2) | BV | 0.35 | 0.65 | 0.65 | 0.65 | 0.65 | 0.65 |

TABLE 12

Inlet/outlet compositions and mass balance

|  |  | Settings 1 | Setting 2 | Setting 3 | Setting 4 | Setting 5 | Setting 6 |
|---|---|---|---|---|---|---|---|
| Feed | SO4 (g/L) | 0.24 | 0.24 | 0.24 | 0.24 | 0.24 | 0.24 |
|  | NH4 (g/L) | 32.4 | 32.4 | 32.4 | 27.7 | 27.7 | 23.6 |
|  | SUCC (g/L) | 55.2 | 55.2 | 55.2 | 61.9 | 61.9 | 49.6 |
|  | Acetate (g/L) | 10.9 | 10.9 | 10.9 | 4.2 | 4.2 | 3.5 |
| Product out (raffinate) | SO4 (g/L) | 43.3 | 62.5 | 62.6 | 63.7 | 63.8 | 57.2 |
|  | NH4 (g/L) | 17.9 | 28.5 | 26.9 | 24.5 | 22.8 | 20.9 |
|  | SUCC (g/L) |  | 6.3 | 3.2 | 8.4 | 4.7 | 2.8 |
|  | Acetate (g/L) |  | 6.0 | 5.3 | 2.7 | 1.05 | 0.07 |
| DF | SO4 (g/L) | 4.0 | 17.6 | 3.3 | 3.6 | 2.7 | 2.6 |
|  | NH4 (g/L) | 5.0 | 1.5 | 1.7 | 1.7 | 1.3 | 1.3 |
|  | SUCC (g/L) | 7.2 | 0.6 | n.a | 0.3 | 0.2 | 1.1 |
|  | Acetate (g/L) |  | 0.5 | n.a | n.a | n.a | 0.005 |
| Regenerant effluents (extract) | SO4 (g/L) | 0.9 | 26.4 | 0 | 0.15 | 0.9 | 0.3 |
|  | NH4 (g/L) | 1.8 | 0.02 | 0.1 | 0.02 | 0.01 | 0.04 |
|  | SUCC (g/L) | 3.3 | 39.2 | 38.1 | 33.7 | 31.9 | 40.8 |
|  | Acetate (g/L) |  | 3.7 | 4.8 | 0 | 0.9 | 0.02 |
| DRG | SO4 (g/L) | 93.4 | 58.5 | 31.5 | 39.1 | 34.1 | 34.8 |
|  | NH4 (g/L) |  | 0.06 | 0.04 | 0.1 | 0.15 | 0.08 |
|  | SUCC (g/L) | 20.4 | 0.3 | 7.7 | n.a | n.a | 1.7 |
|  | Acetate (g/L) |  | n.a | n.a | n.a | n.a | 0.04 |
| Loop (RW1) | SO4 (g/L) | 0.2 | 0.2 | 0.1 | 0.5 | 0.9 | 0.4 |
|  | NH4 (g/L) | 0.2 | 0.1 | 0.04 | 0.5 | 0.5 | 0.4 |
|  | SUCC (g/L) |  | n.a | 0 | 0.4 | 0.2 | 0.3 |
|  | Acetate (g/L) |  | n.a | n.a | n.a | n.a | 0.005 |
| Loop (RW 2) | SO4 (g/L) | 14.8 | 13.1 | 10.9 | 19.9 | 12.8 | 11.6 |
|  | NH4 (g/L) | 0.4 | 1.7 | 2.8 | 4.8 | 2.1 | 1.1 |
|  | SUCC (g/L) |  | n.a | n.a | n.a | n.a | 0 |
|  | Acetate (g/L) |  | n.a | n.a | n.a | n.a | 0.002 |
| Mass balance out/in | SO4 (g/L) | 134 | 150 | 103 | 110 | 110 | 115 |
|  | NH4 (g/L) | 77 | 95 | 93 | 106 | 92 | 95 |
|  | SUCC (g/L) | 62 | 105 | 100 | 87 | 77 | 100 |
|  | Acetate (g/L) | 0 | 102 | 99 | 64 | 55 |  |

"n.a" means that the value is low and could not have been determined with exact precision

TABLE 13

Process performances (Calculated for ten columns)

|  |  | Setting 1 | Setting 2 | Setting 3 | Setting 4 | Setting 5 | Setting 6 |
|---|---|---|---|---|---|---|---|
| Cycle time | Min | 43.5 | 56 | 54 | 53 | 62 | 62 |
| Loading | Eq/L | 0.95 | 0.95 | 0.90 | 0.96 | 0.96 | 0.94 |
| Capacity | Eq/L | 0.95 | 0.84 | 0.85 | 0.83 | 0.89 | 0.89 |
| Succinate recovery | % | 100.0 | 88.7 | 94.3 | 86.4 | 92.4 | 94.4 |
| Regeneration level | Eq/L | 1.875 | 1.875 | 1.5 | 1.5 | 1.5 | 1.5 |
| Regeneration rate | % | 197 | 222 | 176 | 181 | 169 | 169 |
| Consumption H2SO4 (net) | Eq/L | 0.20 | 0.92 | 1.03 | 0.98 | 0.91 | 0.90 |
| Acid conversion | % | −78.1 | 99.8 | 99.4 | 99.8 | 99.9 | 99.7 |

TABLE 14

Continuous ion exchange characteristics

|  |  | Feed | Extract | Raffinate |
|---|---|---|---|---|
| Volume | BV | 1.1 | 1.1 | 1.2 |
| Brix |  | 9 | 3.5 | 9.3 |
| pH | [-] | 7.2 | 2.5 | 2.1 |
| Conductivity | [mS/cm] | 66 | 2.25 | 96 |
| Succinate | g/L | 49.6 | 40.8 | 2.8 |
| Acetate | g/L | 3.5 | 0.02 | 0.07 |
| SO4 | g/L |  | 0.3 | 57.2 |
| NH4 | g/L | 23.5 | 0.04 | 20.9 |

TABLE 15

NF membrane characteristics

| Type |  | Retention rate MgSO4 % | Exchange Surface area M² | Temperature °C. | Pressure bars |
|---|---|---|---|---|---|
| NF | Persep I | Mini 96%<br>Checked: 99.6% | 0.23 | 25-45 | 15 |

TABLE 16

Product evolution during nanofiltration

|  |  | Ion exchange Extract | NF Reten | NF perm | NF ret After Diaf1 | NF perm Diaf1 | NF ret After Diaf2 | NF perm Diaf2 |
|---|---|---|---|---|---|---|---|---|
| Volume | L | 23.45 | 0.75 | 22.45 | 0.7 | 0.7 | 0.7 | 0.7 |
| Cond. | mS/cm | 2.25 | 5.35 | 3 | 4.92 | 2.89 | 4.61 | 2.56 |
| pH |  | 2.5 | 2.3 | 2.4 | 2.4 | 2.5 | 2.4 | 2.4 |
| Brix | % | 3.5 | 4.3 | 3.9 | 3.3 | 2.9 | 2.5 | 2.2 |
| Absorbance 420 nm | OD | 0.035 | 0.3 | 0.005 |  |  |  |  |
| Succinic acid | g/L | 45.5 | 55.2 | 46 | 38 | 39.2 | 27.4 | 28.7 |
| Lactic acid | mg/L | 88.2 | 88.9 | 86.5 | 712 | 714 | 536 | 583 |
| NH4 | mg/L | 38 | 205 | 29 | 197 | 91 | 177 | 83 |
| SO4 | mg/L | 152 | 1374 | 70 | 1273 | 374 | 1214 | 331 |

TABLE 17

Estimated retention rates

|  | Permeate Color | Succinate | | SO4 | | NH4 | | Lactate | |
|---|---|---|---|---|---|---|---|---|---|
| VCF | Optical Density 420 nm | Retent. Rat % | Perme. Fraction. % | Retent. Rate % | Perme Fraction % | Retent. Rate % | Perme. Fraction % | Retent. Rate % | Perme. fraction % |
| 2.0 | 0.001 | 3 | 49 | 90 | 9 | 64 | 23 | −0.4 | 50 |
| 3.1 |  | 8 | 65 | 89 | 19 | 74 | 34 | −0.3 | 68 |
| 4.2 |  | 4 | 74 | 87 | 25 | 72 | 43 | −3.0 | 76 |
| 5.3 | 0.003 | 2 | 79 | 85 | 33 | 69 | 51 | −2.3 | 81 |
| 12.3 | 0.004 | 6 | 91 | 81 | 59 | 66 | 73 | −0.9 | 92 |
| 31.3 | 0.005 | 5 | 96 | 74 | 80 | 58 | 88 | 0.4 | 97 |
| Diaf 1 |  | −3 | 98 | 71 | 84 | 54 | 90 | −0.3 | 98 |
| Diaf 2 |  | −5 | 98 | 73 | 85 | 53 | 91 | −8.7 | 98 |

TABLE 18

Results of succinic acid crystallization trials

| Feed Type | | | Succinate | SO4 | Acetate | K | NH4 | Lactate | Total Weight |
|---|---|---|---|---|---|---|---|---|---|
| Extract from Ion Exchange Chromatography - No Polishing | Feed | g/L | 423.2 | 41.8 | 0.001 | | 3.3 | | |
| | Mother liquor | g/L | 51.9 | 62.3 | 0.15 | | 5.3 | | 1574 |
| | Dried Washed Crystal Purity | % | 99.8 | 0.01 | 0 | | 0.001 | | 1021 |
| | Crystal yield | % | 93 | 0.15 | | | | | |
| Extract from Ion Exchange Chromatography - NF Polishing | Feed | g/L | 426 | 1.97 | 0.09 | 0.1 | 0.62 | 2.65 | |
| | Mother liquor | g/L | 75.9 | 3.07 | 0.14 | 0.06 | 0.88 | 4.14 | 780 |
| | Dried Washed Crystal Purity | % | 99.7 | 0 | 0 | 0.02 | 0.02 | 0 | 1325 |
| | Crystal yield | % | 89 | 0.2 | 0 | 62 | 9.6 | | |
| Synthetic Succinic Acid Solution | Feed | g/L | 420 | 25 | 0 | 0 | 0.4 | 5 | |
| | Mother liquor | g/L | 60.3 | 30.3 | 0 | 0 | 0.4 | 6.21 | 1400 |
| | Dried Washed Crystal Purity | % | 99.85 | 0.14 | 0 | 0 | 0.01 | 0 | 734 |
| | Crystal yield | % | 90 | 2.4 | | | 7.7 | 0 | |
| Commercial crystals sample | Dried Washed Crystal Purity | % | 99.99 | | | | 0.01 | | |

TABLE 19

Table comparison of color of different crystal preparations

| Feed Type | Color | Optical Density at 420 nm (100 g/L solution) |
|---|---|---|
| Concentrated extract – No Polishing | Brown | 0.020 |
| Concentrated extract – After polishing NF | White | 0.007 |
| Synthetic solution | White | 0.002 |
| Commercial crystals sample | White | 0.001 |

TABLE 20

Results of Ammonium crystallization trial

| | | Succinate | Sulfate | Acetate | NH4 | K | Total amount (g) |
|---|---|---|---|---|---|---|---|
| Feed 50 Bx | g/L | 19.6 | 350.0 | | 110.9 | 16.3 | |
| Mother liquor | g/L | 45.4 | 395 | 4.4 | 162.95 | 10.5 | 1657 |
| Dried crystals | % | 0 | 68 | 9 | 27 | 3 | 615 |
| Total crystals | g | | 419.8 | | 166.2 | 17.0 | |
| Total Mother Liquor | g | | 545.4 | | 25.0 | 14.5 | |
| Yield | % | | 43 | | 42 | 54 | |

References

All references are listed herein for the convenience of the reader. Each reference is incorporated by reference in its entirety.

U.S. Pat. No. 5,034,105
U.S. Pat. No. 5,068,418
U.S. Pat. No. 5,068,419
U.S. Pat. No. 5,104,492
U.S. Pat. No. 5,132,456
U.S. Pat. No. 5,143,833
U.S. Pat. No. 5,143,834
U.S. Pat. No. 5,168,055
U.S. Pat. No. 5,412,126
U.S. Pat. No. 5,426,220
U.S. Pat. No. 5,641,406
U.S. Pat. No. 5,770,435
U.S. Pat. No. 5,786,185
U.S. Pat. No. 5,817,238
U.S. Pat. No. 5,958,744
U.S. Pat. No. 6,159,738
U.S. Pat. No. 6,160,173
U.S. Pat. No. 6,265,190
U.S. Pat. No. 6,280,985
U.S. Pat. No. 6,284,904
U.S. Pat. No. 6,319,382
U.S. Pat. No. 6,455,284
U.S. Pat. No. 7,223,567
U.S. Pat. No. 7,238,837
U.S. Pat. No. 7,439,392
U.S. Pat. No. 7,563,606
U.S. Pat. No. 7,763,447
U.S. Pat. No. 7,829,316
U.S. Pat. No. 7,833,763
U.S. Patent Application Publication No. 2006/0276674
U.S. Patent Application Publication No. 2007/011294
U.S. Patent Application Publication No. 2009/0137825
U.S. Patent Application Publication No. 2009/0137843
U.S. Patent Application Publication No. 2010/0184171
U.S. Patent Application Publication No. 2010/0297715
International Patent Application Publication No. WO 89/05861
International Patent Application Publication No. WO 98/30712

International Patent Application Publication No. WO 2007/040458

International Patent Application Publication No. WO 2008/115958

International Patent Application Publication No. WO 2009/08101

International Patent Application Publication No. WO 2009/065778

International Patent Application Publication No. WO 2009/065780

International Patent Application Publication No. WO 2009/082050

International Patent Application Publication No. WO 2010/115067

Bechthold, I., Bretz, K., Kabasci, S., Kopitzky, R., Springer, A. (2008) Succinic acid: a new platform chemical for bio-based polymers from renewable resources. *Chem. Eng. Technol.* 5: 647-654.

Davison, B. H., Nghiem, N. P., Richardson, G. L. (2004) Succinic acid adsorption from fermentation broth and regeneration. *App. Biochem. Biotechnol.* 113-116: 653-669.

Delhomme, C., Weuster-Botz, D., Kuhn, F. E. (2009) Succinic acid from renewable resources as a C4 building-block chemical—a review of the catalytic possibilities in aqueous media. *Green Chem.* 11:13-26.

Hong, Y. K. Hong, W. H. (2000a) Reactive extraction of succinic acid with triprophyamine (TPA) in various diluents. *Bioproc. Eng.* 22:284-284.

Hong, Y. K., Hong, W. H. (2000b) Equilibrium studies on reactive extraction of succinic acid from aqueous solutions with tertiary amines. *Bioproc. Eng.* 22: 477-481.

Hong, Y. K., Hong, W.H. (2000c) Extraction of succinic acid with 1-octanol/n-heptane solutions of mixed tertiary amine. *Biopro. Engineer.* 23: 535-538.

Hong, S. H., Lee, S. Y. (2001) Metabolic flux analysis for succinic acid production by recombinant *Escherichia coli* with amplified malic enzyme activity. *Biotechnol. Bioeng.* 74: 89-95.

Hong, Y. K., Hong, W. H., Chang, H. N. (2010) Selective extraction of succinic acid from binary mixture of succinic acid and acetic acid. *Biotechnol. Lett.* 22: 871-874.

Huh, Y.S., Jun, Y-S., Hong, Y. K., Song, H., Lee, S. Y., Hong, W. H. (2006) Effective purification of succinic acid from fermentation broth produced by *Mannheimia succiniproducens. Process Biochem.* 41: 1461-1465.

Inci, I. (2007) Linear salvation energy relationship modeling and kinetic studies on reactive extraction of succinic acid by tridodecylamine dissolved in MIBK. *Biotechnol Prog.* 23: 1171-1179.

Jantama, K., Haupt, M. J., Svoronos, S. A., Zhang, X., Moore, J. C., Shanmugam, K. T., Ingram, L. O. (2008a) Combining metabolic engineering and metabolic evolution to develop nonrecombinant strains of *Escherichia coli* C that produce succinate and malate. *Biotechnol. Bioeng.* 99: 1140-1153.

Jantama, K., Zhang, X., Moore, J. C., Shanmugam, K.T., Svoronos, S. A., Ingram, L. O. (2008b) Eliminating side products and increasing succinate yields in engineered strains of *Escherichia coli* C. *Biotechnol. Bioeng.* 101: 881-893.

Jun, Y-S., Huh, Y. S., Hong, W. H., Hong, Y. K. (2005) Kinetics of the extraction of succinic acid with tri-n-octylamine in 1-Octanol solution. *Biotechnol. Prog.* 21: 1673-1679.

Kurzrock, T., Weuster-Botz, D. (2010) Recovery of succinic acid from fermentation broth. *Biotechnol. Lett.* 32: 331-339.

Li, Q., Li, W-1., Wang, D., Liu, B-b., Tang, H., Yang, M-h., Liu, Q-f., Xing, J-m., Su, Z-g. (2010) pH Neutrallization while succinic acid adsorption onto anion exchange resins. *Appl. Biochem. Biotechnol.* 160:438-445.

Luque, R., Lin, C. S., Du, C., Macquarrie, D. J., Koutinas, A., Wang, R., Webb, C., Clark, J. H. (2009) Chemical transformations of succinic acid recovered from fermentation broths by a novel direct vacuum distillation-crystallization method. *Green Chem.* 11: 193-200.

Song, H., Huh, Y.S., Lee, S. Y., Hong, W. H., Hong, Y. K. (2007) Recovery of succinic acid produced by fermentation of a metabolically engineered *Mannheimia succiniproducens* strain. *J. Biotechnol.* 132: 445-452.

What is claimed is:

1. An industrial scale continuous process for recovering succinic acid from a fermentation broth containing succinate salt wherein said continuous process comprises the steps of:
    (a) providing (i) a fermentation broth containing succinate salt and (ii) an anionic ion exchange resin;
    (b) contacting the anionic ion exchange resin with the fermentation broth containing succinate salt, which comprises succinate anion and a cation;
    (c) exchanging the succinate anion with the anion on the ion exchange resin;
    (d) washing the ion exchange resin to remove materials other than the succinate anion bound to the ion exchange resin;
    (e) displacing the succinate anion from the ion exchange resin as succinic acid by washing the resin with an acid containing an anion that is stronger than the succinate anion, in a concentration and at a temperature effective to displace the succinate anion without causing crystallization of succinic acid during the ion exchange process; and
    (f) collecting the fractions containing succinic acid;
    wherein said contacting between the ion exchange resin and the fermentation broth is achieved in a continuous ion-exchange mode;
    wherein said succinate salt is selected from the group consisting of ammonium succinate, potassium succinate, sodium succinate and mixtures of two or more thereof;
    wherein said cation is selected from the group consisting of ammonium, potassium, sodium and mixtures of two or more thereof; and
    wherein the concentration of washing acid in step (e) is 5% to 8% (w/w).

2. The process of claim 1 wherein the acid used in step (e) is selected from the group consisting of sulfuric acid, phosphoric acid, hydrochloric acid, and nitric acid.

3. The process of claim 1, further comprising a step of clarifying the aqueous solution comprising ammonium succinate using a method selected from the group consisting of centrifugation, high-temperature treatment, alkaline treatment, microfiltration, ultrafiltration and diafiltration.

4. The process of claim 1 further comprising a step of polishing the recovered succinic acid wherein the recovered succinic acid is filtered through a nano-membrane to achieve decolorization.

5. The process of claim 1, further comprising a step of evaporation wherein the succinic acid fractions collected in step (f) are evaporated to achieve a concentration of at least 100g of succinic acid per liter.

6. The process of claim 1, further comprising a step of crystallization wherein the succinic acid in aqueous form collected in step (f) is converted into crystalline form.

7. The process of claim 6 wherein the crystalline succinic acid is isolated, and has a sulfate concentration of less than 100 ppm.

8. An industrial scale continuous process for recovering a carboxylic acid from a fermentation broth containing a carboxylic acid salt, wherein said continuous process comprises the steps of:
(a) providing a fermentation broth containing a carboxylic acid salt;
(b) contacting said fermentation broth with a basic ion exchange resin by passing the fermentation broth though a column filled with said basic ion exchange resin;
(c) adjusting the volume of said fermentation broth containing said carboxylic acid salt being passed through said column filled with a basic ion exchange resin so that said volume of said fermentation broth is below the level required to saturate said basic ion exchange resin, and there is no breakthrough peak in the elution profile from said column;
(d) splitting said carboxylic acid salt on the surface of said basic ion exchange resin into carboxylate anion plus cation and exchanging the carboxylate anion released from said salt splitting reaction for the anion on the surface of said basic ion exchange resin leading to the formation of a new salt in the aqueous phase;
(e) recovering the newly formed salt in the aqueous solution;
(f) releasing the carboxylic acid and regenerating the ion exchange resin by washing with an acid solution in a concentration and at a temperature effective to prevent crystallization of the carboxylic acid during the ion exchange process; and
(g) recovering the carboxylic acid from acid wash solution;
wherein said contacting between the ion exchange resin and the fermentation broth is achieved in a continuous ion-exchange mode;
wherein said carboxylic acid salt is selected from the group consisting of lactic acid salt, succinic acid salt, citric acid salt, gluconic acid salt, glucaric acid salt, aspartic acid salt and muconic acid salt;
wherein the cationic form of said carboxylic salt is selected from the group consisting of ammonium, potassium, sodium and mixtures of two or more thereof; and
wherein the concentration of washing acid in step (f) is 5% to 8% (w/w).

9. The process for recovering carboxylic acid from a fermentation broth containing carboxylic acid salt as in claim 8, further comprising a step of clarifying said fermentation broth using a method selected from the group consisting of centrifugation, high-temperature treatment, alkaline treatment, microfiltration, ultrafiltration and diafiltration.

10. The process for recovering carboxylic acid from a fermentation broth containing carboxylic acid salt as in claim 8, further comprising a step of polishing recovered carboxylic acid wherein said recovered carboxylic acid is filtered through a nanomembrane to achieve decolorization.

11. The process for recovering carboxylic acid from a fermentation broth containing carboxylic acid salt as in claim 8 further comprising a step of crystallization wherein said recovered carboxylic acid is converted into crystalline form.

12. The process of claim 8 wherein the acid used in step (f) is selected from the group consisting of sulfuric acid, phosphoric acid, hydrochloric acid, and nitric acid.

13. The process of claim 8, wherein at least steps (b) through (f) are performed at a temperature of 50° C.

14. The process of claim 1, wherein at least steps (b) through (e) are performed at a temperature of 50° C.

15. The process of claim 1, wherein the continuous ion-exchange mode is selected from the group consisting of moving port system and moving column system.

16. The process of claim 8, wherein the continuous ion-exchange mode is selected from the group consisting of moving port system and moving column system.

17. An industrial scale continuous process for recovering succinic acid from a fermentation broth containing succinate salt wherein said continuous process comprises the steps of:
(a) providing (i) a fermentation broth containing succinate salt and (ii) an anionic ion exchange resin;
(b) contacting the anionic ion exchange resin with the fermentation broth containing succinate salt, which comprises succinate anion and a cation;
(c) exchanging the succinate anion with the anion on the ion exchange resin;
(d) washing the ion exchange resin to remove materials other than the succinate anion bound to the ion exchange resin;
(e) displacing the succinate anion from the ion exchange resin as succinic acid by washing the resin with 8% sulfuric acid at a temperature of 50° C.; and
(f) collecting the fractions containing succinic acid;
wherein said contacting between the ion exchange resin and the fermentation broth is achieved in a continuous ion-exchange mode; wherein said succinate salt is selected from the group consisting of ammonium succinate, potassium succinate, sodium succinate and mixtures of two or more thereof, and wherein said cation is selected from the group consisting of ammonium, potassium, sodium and mixtures of two or more thereof.

\* \* \* \* \*